(12) United States Patent
Ray et al.

(10) Patent No.: US 6,258,045 B1
(45) Date of Patent: Jul. 10, 2001

(54) COLLECTION DEVICE FOR BIOLOGICAL SAMPLES AND METHODS OF USE

(75) Inventors: Robert A. Ray, Stuart; Robert Stangarone, Boca Raton; Julie Peddicord, Jensen Beach, all of FL (US)

(73) Assignee: FlexSite Diagnostics, Inc.

( * ) Notice: Subject to any disclaimer, the term of this patent is extended or adjusted under 35 U.S.C. 154(b) by 0 days.

(21) Appl. No.: 09/415,304

(22) Filed: Oct. 8, 1999

Related U.S. Application Data

(63) Continuation-in-part of application No. 09/169,843, filed on Oct. 9, 1998, now Pat. No. 6,036,659.

(51) Int. Cl.[7] .................................................. A61B 5/00
(52) U.S. Cl. .............................................................. 600/573
(58) Field of Search ................................. 600/573, 575, 600/584; 604/403, 406; 422/50, 56, 58; 436/74, 169, 170

(56) References Cited

U.S. PATENT DOCUMENTS

| 4,260,392 | 4/1981 | Lee ........................................ 435/22 |
| 4,277,249 | 7/1981 | Broughton ............................. 436/86 |
| 4,299,812 | 11/1981 | Coombes ............................. 436/500 |
| 4,654,127 | 3/1987 | Baker et al. ......................... 205/792 |
| 4,678,757 | 7/1987 | Rapkin et al. ....................... 436/169 |
| 4,738,823 | 4/1988 | Engelmann ........................... 422/56 |
| 4,753,776 | 6/1988 | Hillman et al. ..................... 422/101 |
| 4,774,192 | 9/1988 | Terminiello et al. ................ 436/530 |

(List continued on next page.)

FOREIGN PATENT DOCUMENTS

| 298 10 858 U1 | 9/1998 | (DE) . |
| 0 524 596 A1 | 1/1993 | (EP) . |

OTHER PUBLICATIONS

Guthrie, R., et al., A Simple Phenylalanine Method for Detecting Phenylketonuria in Large Populations of Newborn Infants, Pediatrics 32(3): 338–343 (1963).

Eross, J., et al., Colorimetric measurement of glycoslylated protein in whole blood, red blood cells, plasma and dried blood, Ann. Clin. Biochem., 21L: 477–483 (1984).

Little, et al., Collection of Blood on Filter Paper for Measurement of Glycated Hemoglobin by Affinity Chromatography, Clin. Chem. 42(5): 869–871 (1986).

Voss, et al., Stability and Accuracy Evaluation of a Capillary Collection System for Hemoglobin A1c Speciments, Clin. Chem. 37(6): 988, Abstract 0373 (1991).

Voss, et al., Evaluation of Capillary Collection System for HbA1c Specimens, Diabetes Care 15(5): 700–701 (1992).

Jeppsson, et al., Capillary Blood on Filter Paper for Determination of HbA1c by Ion Exchange Chromatography, Diabetes Care 19(2): pp. 142–145 (1995).

Niederau, et al., Evaluation of a Non–Liquid Transportable Device for Capillary Blood Suitable for HbA1c Determination, Clin. Chem. 42(6): 167, Abstract 0297 (1996).

Little, et al., Filter Paper Collection of Blood for Measurement of HbA1c Immunoassay, Clin. Chem. 42(6): 193, Abstract 0404 (1996).

(List continued on next page.)

*Primary Examiner*—Eric F. Winakur
*Assistant Examiner*—Charles Marmor, II
(74) *Attorney, Agent, or Firm*—Akerman Senterfitt

(57) ABSTRACT

A device for remote-site biological sample collection for laboratory analysis is described. The device can be made in several configurations which all include separate members for collecting and separating the biological sample into its desired components which are detected or measured. Methods of use for the device are also described.

39 Claims, 17 Drawing Sheets

U.S. PATENT DOCUMENTS

| | | | |
|---|---|---|---|
| 4,790,979 | 12/1988 | Terminiello et al. | 422/56 |
| 4,810,394 | 3/1989 | Masuda | 210/767 |
| 4,816,224 | 3/1989 | Vogel et al. | 422/55 |
| 4,845,132 | 7/1989 | Masuoka et al. | 521/53 |
| 4,883,764 | 11/1989 | Kloepfer | 436/63 |
| 4,933,092 | 6/1990 | Aunet et al. | 210/729 |
| 4,987,085 | 1/1991 | Allen et al. | 436/169 |
| 5,004,584 | 4/1991 | Rayman | 422/58 |
| 5,064,541 | 11/1991 | Jeng et al. | 210/767 |
| 5,079,142 | 1/1992 | Coleman et al. | 435/7.92 |
| 5,082,626 | 1/1992 | Grage, Jr. | 422/56 |
| 5,084,173 | 1/1992 | Nitadori et al. | 210/321.89 |
| 5,087,566 | 2/1992 | Ertinghausen | 435/7.9 |
| 5,130,258 | 7/1992 | Makino et al. | 436/169 |
| 5,135,719 | 8/1992 | Hillman et al. | 422/101 |
| 5,139,685 | 8/1992 | de Castro et al. | 210/767 |
| 5,204,267 | 4/1993 | Sangha et al. | 436/14 |
| 5,240,862 | 8/1993 | Koenhen et al. | 436/178 |
| 5,260,221 | 11/1993 | Ramel et al. | 436/169 |
| 5,262,067 | 11/1993 | Wilk et al. | 210/767 |
| 5,264,180 | 11/1993 | Allen et al. | 422/56 |
| 5,266,219 | 11/1993 | Pall et al. | 210/767 |
| 5,340,539 | 8/1994 | Allen et al. | 422/56 |
| 5,415,758 | 5/1995 | Comeau | 204/462 |
| 5,416,000 | 5/1995 | Allen et al. | 435/7.92 |
| 5,427,953 | 6/1995 | Yee | 436/74 |
| 5,432,097 | 7/1995 | Yourno | 436/175 |
| 5,435,970 | 7/1995 | Mamenta et al. | 422/56 |
| 5,460,057 | 10/1995 | Østrup | 73/864.81 |
| 5,460,777 | 10/1995 | Kitajima et al. | 422/56 |
| 5,496,626 | 3/1996 | Hamajima et al. | 422/412 |
| 5,508,200 | 4/1996 | Tiffany et al. | 436/44 |
| 5,516,487 | 5/1996 | Rosenthal et al. | 422/55 |
| 5,597,532 | 1/1997 | Connolly | 422/58 |
| 5,665,238 | 9/1997 | Whitson et al. | 210/649 |
| 5,725,774 | 3/1998 | Neyer et al. | 210/645 |
| 5,772,644 | 6/1998 | Bark et al. | 604/317 |
| 5,795,483 | 8/1998 | Ung-Chhun et al. | 210/645 |
| 5,846,438 | 12/1998 | Pall et al. | 210/767 |
| 5,846,837 | 12/1998 | Thym et al. | 436/170 |
| 5,916,521 | 6/1999 | Bunce et al. | 422/56 |
| 5,922,210 | 7/1999 | Brody et al. | 210/767 |
| 5,922,288 | 7/1999 | Herst | 422/101 |
| 5,948,695 | 7/1999 | Douglas et al. | 436/518 |
| 5,981,294 | * 11/1999 | Blatt | 436/178 |
| 6,001,658 | * 12/1999 | Fredrickson | 436/514 |
| 6,008,059 | 12/1999 | Schrier et al. | 436/518 |
| 6,009,632 | * 1/2000 | Douglas | 33/562 |
| 6,027,943 | * 2/2000 | Kang et al. | 436/518 |
| 6,036,919 | * 3/2000 | Thym et al. | 422/58 |

OTHER PUBLICATIONS

Marsden, et al., The Comparative Performances of Whatman BFC 180 and S&S903 Filter Papers in Newborn Screening Assays for Immunoreactive Trypson, 17–OHP and Galactose, Third Meeting of the International Society for Neonatal Screening and the 12th National Neonatal Screening Symposium, Boston, Massachusetts (Oct. 21–24, 1996).

Vohra, et al., Efficacy of New Filter Paper in a State Newborn Screening Program, Third Meeting of the International Society for Neonatal Screening and the 12th National Neonatal Screening Symposium, Boston, Massachusetts (Oct. 21–24, 1996).

Duddy, et al., The Evaluation of Whatman BFC180 Blood Collection Paper Against Two Alternative Products, Third Meeting of the International Society for Neonatal Screening and the 12th National Neonatal Screening Symposium, Boston, Massachusetts (Oct. 21–24, 1996).

* cited by examiner

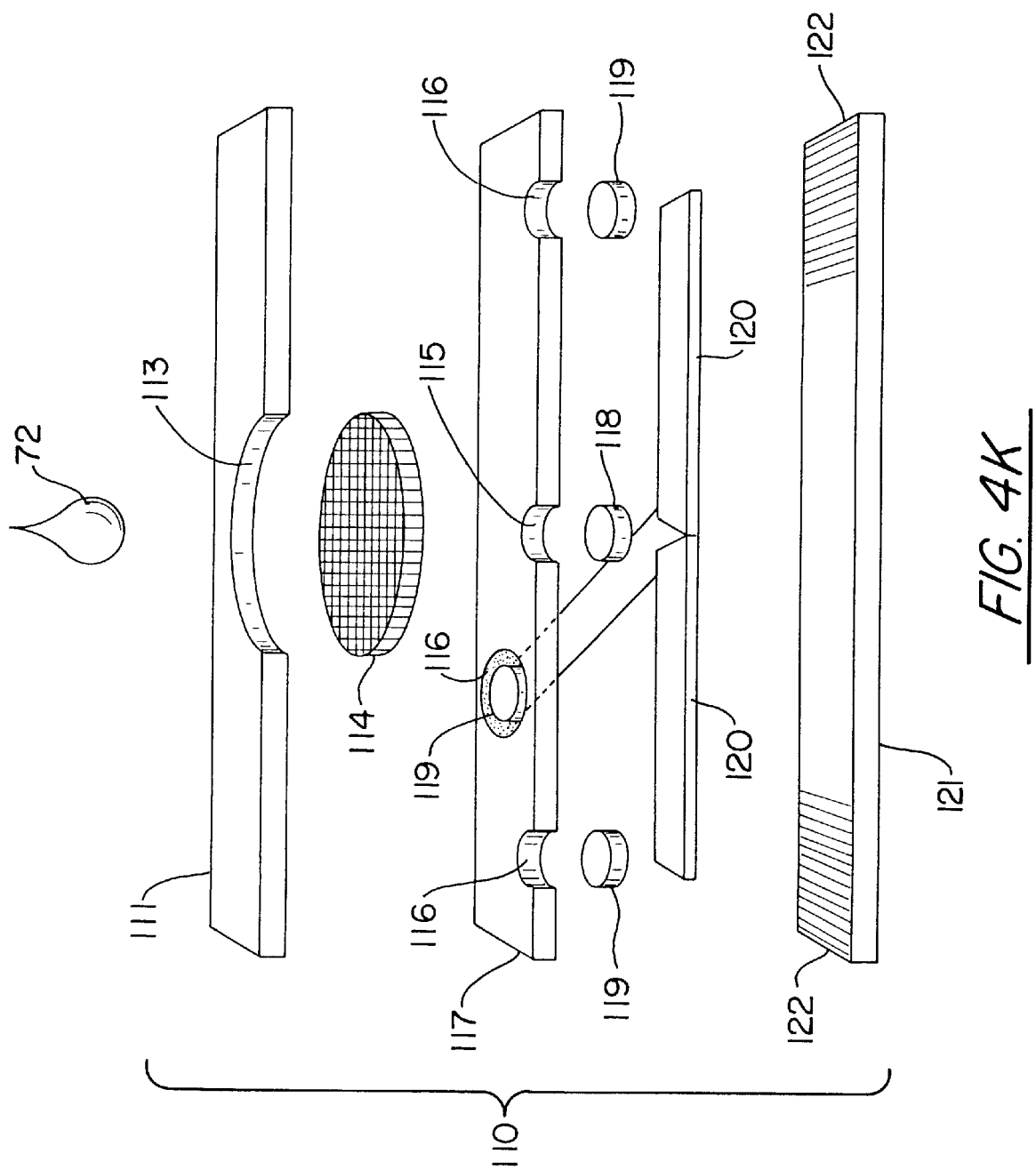

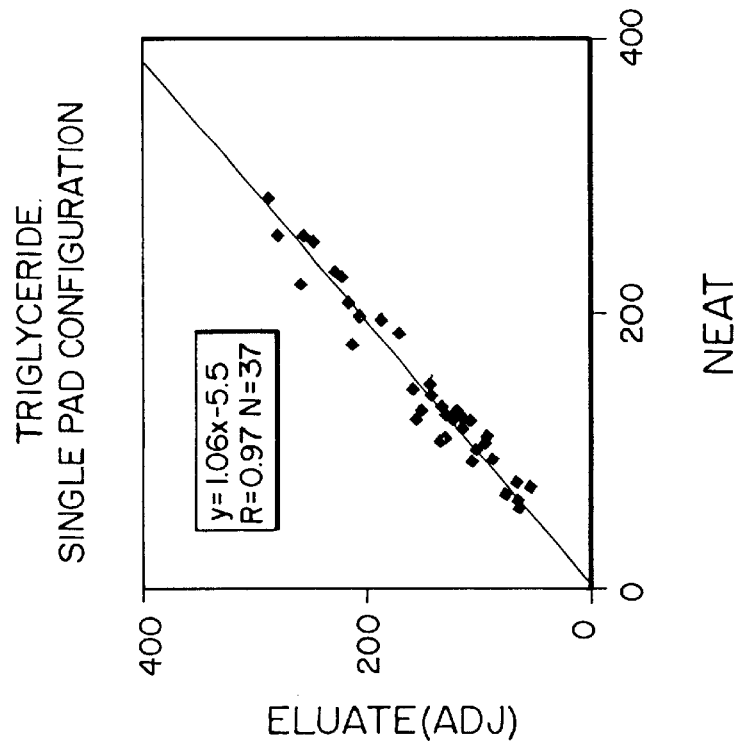
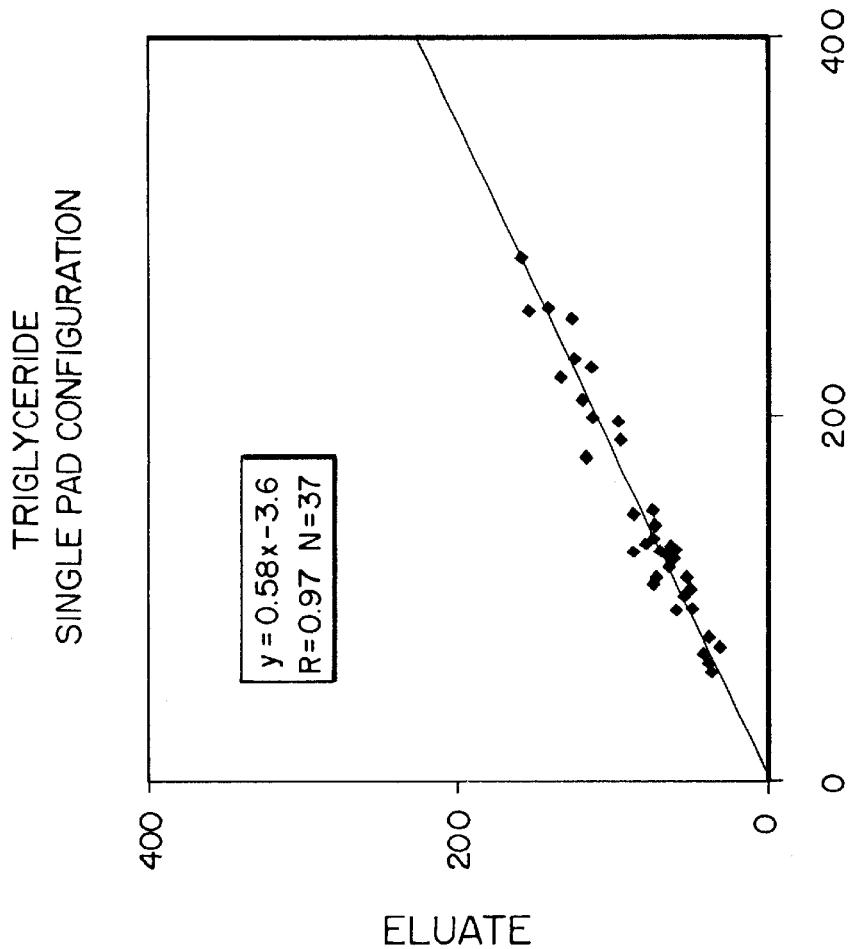

COLLECTION DEVICE FOR BIOLOGICAL SAMPLES AND METHODS OF USE

CROSS REFERENCE TO RELATED APPLICATIONS

The present application is a continuation in part of U.S. application Ser. No. 09/169,843 filed Oct. 9, 1998, now U.S. Pat. No. 6,036,659, which is incorporated herein by reference.

BACKGROUND OF THE INVENTION

The subject invention relates to a device and method for collection, transport, storage, processing (e.g., separation of cells from serum), and compatibility with laboratory analysis of a biological sample obtained from a living organism. In particular, the subject invention relates to a device and method used in the analysis of a biological component in a dried blood or urine sample obtained from an animal.

In laboratory and clinical settings, it is often necessary to take, contain, transport, and store biological samples, such as blood or blood products, for purposes of analysis of various components in the sample. The analysis of biological fluids to confirm the levels or concentrations of various components contained therewithin is an accepted clinical practice for the determination of proper functioning of various biological systems. Liquid sample collection, handling, transport, and storage, which is the conventional approach, has many problems associated with it including: (1) the risk of container breakage or leakage which causes loss of sample and the danger of infection; (2) sample instability during shipment and storage; (3) refusal of transport carriers to accept liquid biohazardous shipments; and (4) collection of more sample than is necessary for testing, to ensure quantities compatible with common laboratory methods of serum or plasma preparation and subsequent analysis.

To overcome these problems, in one approach, a biological sample, e.g., a drop or two of whole blood, has been collected on filter paper and dried prior to transport. These dried blood spot samples are mailable and are accepted by all common carriers. Despite the improved handling of dry samples, however, analysis of certain dissolved blood components is not currently possible from a whole blood sample unless the red blood cells are first separated from the blood plasma or serum. The most conventional manner of separating serum or plasma from blood cells is by centrifugation.

In the case of certain blood component determinations, the handling of the blood samples can also be a critical part of the ultimate accuracy of measurement in the sample. Therefore, even when a blood sample is removed from the body, the concentration of the component within a liquid blood sample can change over time. Dried blood spots have the advantage of helping to preserve certain components for later analysis.

There is currently a need for a simple, yet accurate device for collection, transport, preparation, and storage of a dried blood plasma or serum sample from whole blood, for subsequent extraction and analysis of components in the dried plasma or serum sample. Testing in the laboratory affords more sophisticated equipment, highly trained personnel, professional quality control, and cost effective solutions.

BRIEF SUMMARY OF THE INVENTION

The subject invention concerns a device for use in collection, separation, stabilization, preservation, transport, storage, and elution of a biological sample for laboratory analysis of particular components in the sample, methods of use for the device, and kits comprising the device.

Specifically, the subject invention concerns a device which is useful for collection of a whole blood sample, allowing separation of the blood cells from the blood serum or plasma, drying the blood serum or plasma sample on the device, transporting the collected and dried blood serum or plasma sample to a laboratory or other facility for analysis, and extracting an analyte of interest from the sample for determining presence or absence of the analyte or, if present, the concentration thereof.

Briefly, one embodiment of the subject device comprises a plurality of separate components, including a quantitation member for facilitating delivery of a particular volume or amount of sample to a collection member. The sample can also be passed through another component, e.g., a separation member which can separate certain undesirable components from the components of interest in the sample. For example, blood cells, e.g., red blood cells, can be separated from blood plasma or serum containing an analyte which is to be tested for, or measured. The collection member, which can be an absorbent or non-absorbent filter or membrane material, can serve to collect the component of interest in the sample, e.g., serum or plasma, provide a surface for drying of the component of interest, and a means for storage of that component for subsequent transport to, and analysis in, a laboratory. The device can have a plurality of any one of the quantitation, separation, or collection members.

One preferred embodiment has a plurality of separation members, including one which also can be useful as a quantitation member. Specifically, the quantitation member serves to collect overflow of sample so that a defined volume of sample component of interest is delivered to the collection member, over which the other described members are superimposed. For example, the separation/overflow member can be a track etched membrane, as is well-known in the art, or can be a screen material which can spread the liquid sample such that a particular volume of the sample is provided in each cell of the screen. This embodiment is termed the "multilaminate configuration."

In one such embodiment of the multilaminate configuration, namely, the "trilaminate configuration," a separation member is contactingly disposed above or below a layer of material which provides a spreading or quantitative effect for the separated serum or plasma. The separated serum or plasma then absorbs into or adsorbs onto a collection member disposed below the spreading or quantitative material and the separation member. Thus, the trilaminate configuration comprises a substantially three-layered collection device, having a separation member, a quantitation member, and a collection member.

Alternatively, in certain embodiments of the subject invention, the quantitation member can be a material having a wicking property, e.g., standard capillary tube such as is used in routine laboratory work (typical volumes are 5–50 microliters), or can be an absorbent or non-absorbent material which has quantitative liquid volume properties for liquids, or an encased fiber bundle or other like configuration which accepts a quantitative liquid uptake and can deliver a predetermined volume of sample to another component of the device.

The separation member can be an absorbent, adsorbent, non-absorbent, or non-adsorbent material, for delivering the sample to the serum/plasma collection member via capillary action. The separation member can also provide a separation function for selectively separating different components within the sample, or can provide a quantitative volumetric measurement function. The separation member, useful for separating a component of interest from an undesired component in the biological sample prior to introduction of the component of interest to the collection member, according to one embodiment, can be a substantially circular section of absorbent filter paper having a predetermined standard size.

In one embodiment, a device according to the subject invention comprises a first wicking or quantitation member and a second "separation member," as described. A third "collection member" component is substantially circular and disposed in contact with the separation member for collecting sample therefrom. Preferably, a device of this embodiment is configured to include a substantially circular collection member contacting a substantially circular separation member which is contactingly disposed between the quantitation or wicking member and the circular collection member. This configuration is referred to herein as a "dual pad" configuration.

The members, namely, the quantitation member, the separation member, and the collection member, must contact one another for transferring the sample from one member to the other. These members can be abutted to one another, can overlap, or can be superimposed over one another. The separation member and collection member are typically substantially similar in diameter; the separation member which also serves as an overflow quantitation member can be substantially the same size or larger in diameter than the collection member. The separation and collection members can have thicknesses, absorbencies, or migration or other physical properties different from one another in order to produce a particular desired effect or result.

In an alternative embodiment, the quantitation member is typically a capillary tube, the separation member is typically a substantially circular section of absorbent filter or chromatography paper having cell separating properties and a predetermined, standard size; and the collection member is an elongate strip of absorbent material, e.g., filter chromatography paper. Thus, the subject device, having the circular separation member and elongate collection member in contact with one another, is configured having two "stems" or "handles" diametrically opposed to one another. This configuration is termed the "single pad" configuration. This embodiment is used by obtaining a small amount of a biological sample to be tested, e.g., a drop of blood from a sterile lancet fingerstick, and bringing the sample in contact with the wicking or quantitation member. The sample then wicks into the separation member and separates into particular components whereby the components of interest migrate to and are retained on the elongate collection member.

In another alternative configuration, termed the "lateral flow configuration," the quantitation or wicking member can be eliminated. The sample, e.g., whole blood, is applied directly to the separation member, and the collection member achieves quantitation by uniformly distributing the serum or plasma in the collection member so that a fixed area of collection member contains a quantitative amount of serum or plasma. A collector of absorbent material, e.g., HemaSep L (Gelman), or a non-adsorbent screen, such as Nitex 3-8/1 (Tetko), can function in such a manner.

For each of these configurations or embodiments, it is preferred to include a cover for at least the collection member and, more preferably, a cover which substantially envelopes the separation member and collection members, except for an aperture or perforation through which the separation member communicates with the outside environment. This aperture further provides a means for applying a liquid sample directly to the separation member if desired. In the case of the dual pad configuration, it is preferable to provide a cover over the separation and collection members, with a perforation or aperture provided over the separation member.

Preferably, the cover comprises a pair of plastic sheets which are superimposed over one another to form a laminated device. At least one of the sheets can have adhesive disposed on one of its facing surfaces so that the sheets can be adhered together around substantially the entire perimeter of the separation and/or collection members. The quantitation or wicking member can extend from the laminated sheets, forming an uncovered "tail". In a preferred embodiment, one of the sheets covering the dual pad configuration is perforated to allow air to reach the separation member to facilitate drying of the sample-saturated separation member prior to transport of the collected sample to a facility for analysis. This advantageously can prevent spillover or undesired migration of separated components, e.g., red blood cells, retained in the separation member to the collection member.

In certain embodiments, at least one additional layer of plastic sheet can be disposed between two members of the device. For example, in one embodiment of the multilaminate configuration, a layer of plastic sheet is disposed between opposing faces of a screen member and a separation member.

The plastic layer so disposed must provide a means for allowing fluid communication between the screen and separation member. Thus, an aperture or pore can be provided to allow sample to migrate from one member to another member, including the collection member.

A centered aperture or pore in this additional plastic layer, wherein the aperture or pore is substantially smaller than the surface area of the receiving face of a juxtaposed separation member, can facilitate directly the sample to that juxtaposed member and can control volume of sample ultimately received by the collection member.

Also within the invention is a "bridge-strip" type device or apparatus for isolating an analyte from a blood sample. In general, this apparatus features a separation member for receiving a portion of the blood sample, the separation member having a filter that selectively retains cellular components contained within the portion of the blood sample and delivers non-cellular components of the portion of the blood sample containing the analyte; a wicking bridge fluidly connected to the separation member such that the wicking bridge can receive the non-cellular components of the portion of the blood sample containing the analyte from the separation member, the wicking bridge including a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants (e.g., chemical or biological reagents) for analyzing the analyte and including a swatch of material that is adapted for absorbing and retaining a specific quantity of the non-cellular components of the portion of the blood sample containing the analyte.

In some variations, the separation member has a layer of glass fiber filter material and a layer of track-etched membrane. The layer of track-etched membrane can be composed of polyester and/or polycarbonate and have a plurality of pores having a mean diameter of about 0.2 to 5.0 micron (e.g. one micron). In addition, the separation member can be impregnated with a surfactant such as polyoxyethylene sorbitan ester (e.g., Tween-20). The separation member can also be impregnated with a protein that reduces adsorption of components of the blood sample to the separation member. For example, the protein can be bovine serum albumin.

The apparatus can also include a separation member that is impregnated with an erythrocyte agglutinin such as a lectin or an antibody that specifically binds to erythrocytes. And the wicking bridge of the apparatus can take the form of a fibrous polyester matrix.

In some embodiments of the apparatus, the quantitative collection member can include a layer of glass fiber filter material, a layer of nylon, and/or a layer of cellulose. The apparatus can also include a second and/or a third quantitative collection member, the second and third quantitative collection members being fluidly connected to the wicking bridge such that the second and third quantitative collection member can receive the non-cellular components of the portion of the blood sample containing the analyte from the wicking bridge, substantially free of any reactants for analyzing the analyte, and comprised of a swatch of material that is adapted for absorbing and retaining a specific quantity of the non-cellular components of the portion of the blood sample containing the analyte.

In yet another embodiment, the apparatus further features an application member fluidly connected to the separation member, the application member including a swatch of material having a plurality of pores for absorbing the blood sample and delivering a portion of the blood sample to the separation member. The application member can be composed of polyester and can be impregnated with a protein (e.g., bovine serum albumin) that reduces adsorption of components of the blood sample to the application member. The application member can also be impregnated with a surfactant such as a polyoxyethylene sorbitan ester, and/or an erythrocyte agglutinin such as a lectin and/or an antibody that specifically binds to erythrocytes.

Some embodiments of the apparatus further include a casing which houses the application member, the separation member, the wicking bridge, and the quantitative collection member. The casing can have an opening for applying the blood sample to the application member. The casing can, for example, have two pieces of a fluid impermeable plastic material sealed together in an airtight manner such that gas exchange between the ambient atmosphere, the application member, the separation member, the wicking bridge, and the quantitative collection member occurs almost entirely through the opening of the casing.

The apparatus can further feature an impermeable spacer interposed between the wicking bridge and the application member, the impermeable spacer can have a thickness of about 0.5 mm (0.020 inches), a first perforation through the thickness for accommodating the separation member, and a second perforation through the thickness for accommodating the quantitative collection member(s). In some variations of this apparatus, the first perforation and the second perforation each have a diameter of about 4.75 mm (0.1875 inches), and the separation member and the quantitative collection member each have a diameter of about 4.65 mm (0.1825 inches). In some embodiments of these variations, the application member can include polyester impregnated with at least one protein that reduces adsorption of components of blood sample to the application member and at least one agglutinin; the separation member can include a layer of glass fiber filter material and a layer of polyester track-etched membrane; the wicking bridge can include a fibrous polyester matrix; and the quantitative collection member can include a layer of nylon and a layer of glass fiber filter material.

The various versions of the apparatus of the invention can also have an identification label attached to the casing, the identification label for displaying information indicating the source of blood sample. The identification label can include a bar code.

The invention additionally features another apparatus for isolating an analyte from a blood sample. This apparatus includes a capillary tube for quantitatively aspirating a specific volume of the blood sample and delivering a specific volume of a portion of the blood sample to the separation member; a separation member fluidly connected to the capillary tube such that the separation member can receive the specific volume of the portion of the blood sample from the capillary tube, the separation member comprising a filter that selectively retains cellular components of the portion of the blood sample and delivers non-cellular components of the portion of the blood sample containing the analyte; a wicking bridge fluidly connected to the separation member such that the wicking bridge can receive the non-cellular components of the portion of the blood sample containing the analyte from the separation member, the wicking bridge comprising a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants for analyzing the analyte and comprising a swatch of material that is adapted for absorbing and retaining a specific quantity of the non-cellular components of the portion of the blood sample containing the analyte.

The subject method begins with the application of a sample, e.g., a drop of whole blood (or "blood spot"), typically procured by a fingerstick using a lancet, to the device by bringing the sample into contact with a quantitation member, an application member, or a separation member, allowing certain components of the sample to selectively migrate to the collection member, and drying the collection member containing the collected sample or allowing it to dry by exposure to air over a period of time, e.g., overnight. The dried sample then can be mailed to the analytical laboratory for determination of presence, absence, or quantity of analyte present in the sample.

Upon receipt of the sample, the analytes contained by the collection member can be physically separated or extracted from the collection member and used for quantitative or qualitative analysis of one or more of those analytes. Advantageously, the subject device can perform at least two functions: (1) as a blood collection means and (2) as a blood transport medium for subsequent clinical analysis.

One objective of this invention is to eliminate problems encountered with currently used devices or methods, including providing a device and method wherein variation of sample size is minimized when absorbed onto a filter paper.

Another object of this invention is to provide for satisfactory drying of the sample prior to packaging and transport of the sample to a laboratory or other facility for analysis.

The subject invention further concerns a kit for enabling an individual to collect a sample and transport it to a facility for analysis. In general, the kit, comprising at least one of the above-described devices and instructions for use of the device, can further include components selected from the following: lancet, antiseptic swab, transport packaging, or an information card for providing information, e.g., medical history or health status, of the individual being tested. For example, the invention features a kit for isolating an analyte from a sample of blood, the kit including an apparatus having a separation member for receiving a predetermined volume of the blood sample, the separation member including a filter that selectively retains cellular components of the portion of the blood sample and delivers non-cellular components of the portion of the blood sample containing the analyte; a wicking bridge fluidly connected to the separation member such that the wicking bridge can receive the non-cellular components of the portion of the blood sample containing the analyte from the separation member, the wicking bridge comprising a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants for analyzing the analyte and comprising a swatch of material that is adapted for absorbing and retaining a specific quantity of the non-cellular components of the portion of the blood sample containing the analyte; and a quantitative fluid dispenser for delivering the predetermined volume of the sample of the blood to the separation membrane. The quantitative fluid dispenser can, for example, take the form of a micropipet or a capillary tube.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 4K shows an exploded perspective view of a bridge strip configuration of an embodiment of the subject invention having three quantitative collection members and three wicking bridges.

FIG. 11 shows regression analysis results for blood sample eluates vs. neat blood samples analyzed for triglyceride concentration using a single pad configuration of a device according to the subject invention.

FIG. 12 shows regression analysis results for blood sample eluates (adjusted) vs. neat blood samples analyzed for triglyceride concentration using a single pad configuration of a device according to the subject invention.

DETAILED DESCRIPTION OF THE PREFERRED EMBODIMENTS

The subject invention concerns a device which can be useful for collection, separation, stabilization or preservation, transport, storage or elution, of components of interest in a biological sample for laboratory analysis of an analyte contained in that sample component. The subject device comprises a separation member for separating and retaining, without leaching from the separation member, an undesired component (e.g., cells), from a component of interest (e.g., serum or plasma) that constitute the sample. The particular component of the sample which is to be analyzed is termed an analyte, which is typically contained within, and is collected with, the component of interest, namely, serum or plasma in a sample of whole blood.

For purposes of this invention, the terms "serum" or "plasma" can be used interchangeably and would be understood by those of ordinary skill in the art to refer to a blood sample having certain cellular components removed or separated therefrom. The serum or plasma containing the analyte selectively migrates through the separation member and becomes retained or "collected" in a second component of the subject device, namely, an absorbent or non-absorbent collection member.

The collection member comprises a membrane on which the sample can be collected, stored, or transported, and further can be eluted or analyzed therefrom. Preferably, the collection member is a material which allows the analyte to be extracted or eluted from the membrane using standard chemistry procedures for subsequent quantitative or qualitative analysis.

Figure 1:
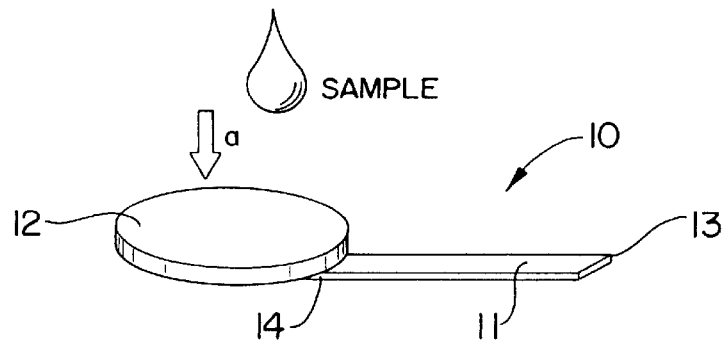
FIG. 1 shows a perspective view of one embodiment ("lateral flow" configuration) of a device according to the subject invention.

A first embodiment for the subject invention is shown in FIG. 1 wherein the device 10 comprises a collection member 11 having a first free end 13 and a second end 14 contacting a separation member 12. The collection member 11 and separation member 12 preferably contact one another in an overlapping manner so that a sample placed onto the separation member 12 can migrate, e.g., via capillary action, toward the collection member 11 so that analyte in the sample, selectively separated from an undesired component, is delivered to, and absorbed into, the collection member. Most preferably, the collection member is positioned to overlap with the separation member wherein the second end of the collection member contacting the separation member is disposed approximately in the center of the separation member. The opposite or free end of the collection member is allowed to extend away from the separation member to form a "tail".

In one embodiment, the separation member can be pre-saturated or pre-treated with a reagent which facilitates separation of an undesired component in the sample from the component of interest which can contain analyte. For example, in a device of the subject invention useful for collection, storage, transport, or analysis of a blood plasma or serum analyte, the separation member can be pre-treated with a reagent which retards migration of red blood cells or a reagent such as a surfactant (e.g., a polyoxyethelene sorbitan ester such as Tween-20) which facilitates flow of sample through the separation member. For a serum analyte, for example, a reagent which agglutinates red blood cells can be used to pre-treat the separation member in the sample, so that a clotting cascade is initiated in a whole blood sample placed on the separation member, retarding movement of the red blood cells to the collection member so that blood serum containing an analyte of interest first reaches and substantially saturates the collection member.

This advantageously eliminates the need to separate serum from a whole blood sample by more labor-intensive methods, e.g., by centrifugation.

In a most preferred embodiment for use with a whole blood sample, the separation member can be pre-treated with a red blood cell agglutinating reagent (i.e., agglutinin) to facilitate separation of the red blood cells from the blood serum. The agglutinin can be, e.g., a lectin such as concanavalin A or the like, or an antibody that specifically binds erythrocytes such as a polyclonal rabbit anti-human erythrocyte antibody preparation. Agglutinins are typically added to the separation member in an amount sufficient to agglutinate most of the erythrocytes in the applied sample, e.g., usually less than 1% concentration by weight (agglutinin: applied sample). As migration of red blood cells is slowed through the separation member 12, serum which can contain an analyte of interest can continue to migrate through the separation member 12 and onto collection member 11 whereby the collection member can become at least partially or, preferably, substantially saturated with serum for subsequent analysis.

It would be understood by those of ordinary skill in the art that other reagents which selectively bind or retard movement of certain other biological sample constituents can also be used for pre-treating the separation member. For example, the separation member can be pre-treated with a reagent which separates unclotted red blood cells from plasma so that plasma proteins, e.g., clotting factors, can be measured or analyzed. Alternatively, a material can be used for the separation member which can selectively separate biological sample components by their biological, chemical, or physical properties. Other reagents that non-specifically reduce adsorption of components of the blood sample to the separation member can be used to pretreat the separation member. For instance, the separator member can be treated with a protein such as albumin (e.g., bovine serum albumin).

Figure 2:
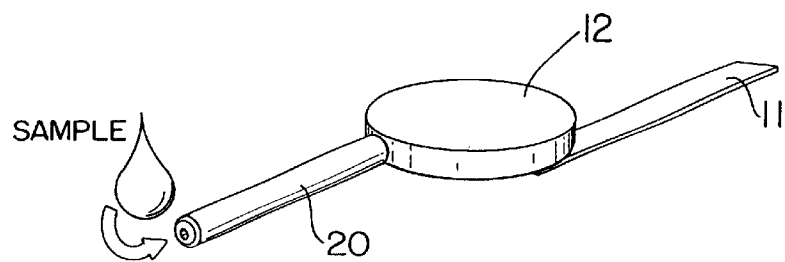
FIG. 2 shows a perspective view of an embodiment of the device according to the subject invention, termed the "single pad" configuration.

The single pad configuration of the subject invention, as shown in FIG. 2, comprises a separation member 12 and collection member 13 as described for the lateral flow configuration. However, this configuration further comprises a quantitation or wicking member 20 which can quantitatively load the sample onto the separation member. The wicking member is preferably a capillary tube which can advantageously provide a means for delivering a specific volume of sample to the collection member. The inner wall of the capillary tube quantitation or wicking member can be coated with an anti-coagulant for facilitating migration of a whole blood sample through the separation member to the collection member.

Figure 3:
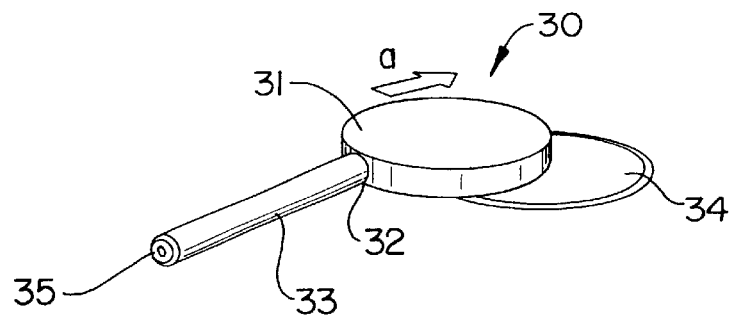
FIG. 3 shows a perspective view of a second embodiment (dual pad configuration) of a device according to the subject invention.

In a further embodiment of the subject invention, as shown in FIG. 3, the "dual pad" configuration of the subject device 30, comprises separation member 31, which is preferably abutting the second end 32 of capillary tube quantitation or wicking member 33, and is overlappingly in contact with the collection member 34. In this configuration, the sample is collected at the free end 35 of wicking member 33 and migrates by capillary action to separation member 31.

Preferably, the capillary tube volume is matched to the absorption capacity of the collection member. For example, we have identified that a capillary volume of about 30 µl is preferred to saturate, but not over-saturate, a collection member of certain materials. Specifically, a 20 µl capacity capillary tube will adequately saturate a 0.48 cm (3/16 inch) diameter collection member with sample, but does not sufficiently saturate a 0.635 cm (1/4 inch) diameter collection member; optimal saturation of a collection member was obtained using a 30 µl capacity capillary tube for an approximately 0.635 cm (1/4 inch) diameter collection member of Ahlstrom 319.

Preferably, the separation member 31 can separate sample constituents in a lateral direction (in a direction from the quantitation or wicking member, as shown by arrow a in FIG. 3) such that migration of undesired constituents, e.g., red blood cells, is retarded, allowing lateral passage of components of interest, e.g., analytes, to migrate onto collection member 34, which is at least partially overlapped by the separation member 31.

A variety of materials can be used for the separation member. These materials are preferably selected from glass fiber, glass fiber/cellulose mixtures, cellulose, or other proprietary materials, including synthetic materials, e.g., nylon.

Useful glass fiber materials include GF-24, GF-25, and #33, available from Schleicher & Schuell (Keene, N.H., USA); G143, G144, and G167, available from Ahlstrom (Mount Holly Springs, Pa., USA); GFQA30VA, GF/P 30, GF/DE 30, GF/SE 30, GF/CM30VA, GF/CM 30, F 075-14, GF DVA, GFVA 20, and GD-2, available from Whatman (Fairfield, N.J., USA); G 40, available from Micron Separation, Inc. (Westborough, Mass., USA); AP 25 and APFD, available from Millipore (Bedford, Mass., USA); and GC-90 and GA-200, available from Osmotics.

Useful glass fiber/cellulose mixture materials include F255-07 90 glass/10 cellulose, F255-09 70 glass/30 cellulose, F255-11 50 glass/50 cellulose, and F255-12 50 glass/50 cellulose, available from Whatman.

Useful cellulose materials include 598, available from Schleicher & Schuell. Miscellaneous or other materials falling outside the above categories can also be used, including HemaSep V and Leukosorb; which article of manufacture according to the subject invention available from Pall BioSupport (Port Washington, N.Y., USA).

One useful nylon material is Nylon 6.6 Transfer Membrane, which is commercially available under the tradename Biodyne B (Pall Specialty Materials, Port Washington, N.Y.). Another useful separation member is a track-etched membrane having pores of mean diameter between 0.2 and 5.0 µm. One such track-etched membrane is available from Whatman and commercialized under the tradename Cyclopore (e.g., Cyclopore PET 1.0 µm pore size).

The separation member of the dual pad configuration can be selected from a variety of materials, including those described for the separation member used in the single pad configuration. In addition, the material known as "PlasmaSep", available from Whatman, can be used.

In one preferred embodiment, the separation member comprises an absorbent chromatography membrane or filter paper, e.g., HemaSep V (Pall BioSupport), which can separate constituents of a biological sample by size or binding characteristics which are well known in the art. The separation member is typically a substantially circular membrane, but is not limited by shape. HemaSep V is well-documented for its vertical separation characteristics (in the direction shown by arrow a in FIG. 1) and can be useful in the lateral flow configuration to separate serum or plasma from undesired sample constituents (cells) in the vertical direction such that serum or plasma flows downward from the top face of the separation member and onto the collection member contactingly disposed on the bottom face of the separation member. In the single and dual pad configurations, a preferred separation member selectively separates serum or plasma from undesired sample components (cells) in a lateral direction, i.e., in the direction of flow from quantitation or wicking member to collection member. HemaSep L (Pall BioSupport) can also be used for this separation member. Preferably, constituents which are not desired to be analyzed (e.g., cells) are substantially bound or retained in the separation member, whereas an analyte in serum or plasma, is allowed to freely or selectively move with the separated plasma or serum through the membrane to the collection member.

The collection member used in the lateral flow configuration can be made from a variety of materials, including cellulose, polypropylene, nylon (including single or multi filament screens), polyester, modified polyester, polyethersulfone, nitrocellulose, high density polyethylene (HDPE), composites of natural and synthetic fibers.

Specifically, these materials can include DE81 and C/CM30, available from Whatman; 5 µm and 10 µm polypropylene, available from Millipore; Magna R 5 µm pore size Magna R 1.2 µm pore size, and 5 µm pore size, available from Micron Separation, Inc.; Loprodyne, HemaSep L, Accuwick 14-20, Accuwick 27-33, Accuwick 42-47, Predator, and Predator (plastic backed), available from Pall BioSystems; Biodyne B (e.g., 0.45 µm) available from Pall Gelman; Cytosep 1660, Cytosep 1661, Cytosep 1662, and Cytosep 1663, Ahlstrom 319 available from Ahlstrom; X-4588, available from Porex; Nitex 3-8/1, Nitex 3-10/1, Nitex 3-15/5, Nitex 3-20/14, and 7-11F/826, available from SEFAR (Charlotte, N.C.; formerly Tetko).

In a preferred embodiment for a single pad or lateral flow configuration, the absorbent collection member is formed as an elongate or rectangular strip of material at least approximately 2 mm in width by at least about 10 mm in length. These dimensions are optimized to be capable of absorbing the total volume of separated sample. More preferably, the absorbent collection member is between about 3–5 mm in width and between about 25–45 mm in length. Most preferably, the absorbent collection member is about 4 mm in width by about 35 mm in length. The most preferred embodiment (4 mm×35 mm) of the collection member provides for an appropriate amount of liquid sample, e.g., a single drop of blood, to saturate but not over-saturate the collection member. Over-saturation occurs when the liquid front of the separated sample reaches the end of the strip, which can result in the analyte bunching up at the tip of the strip, making elution or analysis more difficult or inconsistent.

The collection member can also be pre-treated with a preservative or stabilizer to enhance stability or "shelf-life" of the separated sample or can be treated with a reagent to facilitate the release of the analytes from the member during the elution process. For example, devices intended for use in a protein assay can include a collection pad that is pre-treated with a reagent formulated to improve the stability of a protein in the sample. Other preservatives or stabilizers that can be used in the subject device include antioxidants, carbohydrates, buffers, other proteins, or the like, which are known in the art to provide a preservative or stabilizing effect on a biological sample. The release of the analytes from the collection pad can be enhanced with a pre-treatment of the collection member of a variety of surfactants.

In yet another alternative of the lateral flow configuration, the flow of sample applied to the device can be reversed, i.e., by applying sample to an elongate separation member. In this configuration, the elongate separation member can comprise an absorbent material capable of selectively retaining undesired sample component, e.g., red blood cells, and allowing fluid (serum or plasma) containing a component of interest to migrate to, and absorb into, a circular collection member.

For this configuration, it is preferred to use a known lateral flow membrane for the separation member. For example, GF-24 (Schleicher & Schuell) can be used and has been identified as a preferred separation member. As described, the separation member can be pre-treated with other reagents, e.g., surfactants to facilitate flow of sample through the member.

For the collection member, useful materials for the dual pad configuration include those described for use in the single pad configuration. In addition, certain highly absorbent materials were identified as providing advantageous results in the dual pad configuration. For example, Gelman Accuwick 14, Whatman BSM (also termed "PlasmaSep"), S&S 903, and Ahlstrom 319 can provide advantageous results.

Figure 4A:
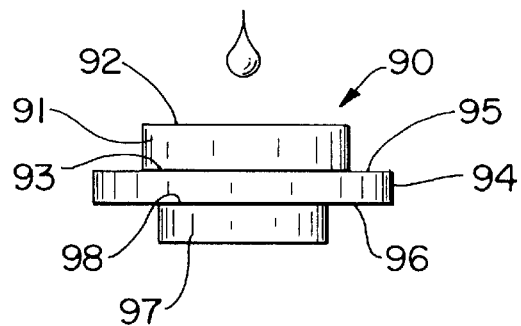
FIG. 4A shows a side view of a third embodiment (trilaminate variation of a multilaminate configuration) of a device according to the subject invention.

A still further embodiment of the subject invention concerns a multilaminate configuration which includes a separation member and quantitation member disposed directly over a collection member. One variation of this configuration is a trilaminate device shown in FIGS. 4A–4E. In FIG. 4A, a side view of the subject device in a trilaminate configuration 90 is shown. This configuration comprises a separation member 91 which is preferably a substantially flat, substantially circular disc made from material as described herein for a separation member. The separation member 91 has an upper face 92 for disposing a drop of biological sample, e.g., blood, thereon. The separation member 91 has a second face 93 which contacts the quantitation member 94 on its top face 95. A bottom face 96 of the quantitation member 94 is disposed so that it contacts the collection member 97. The collection member 97 can be an absorbent material as previously described.

This particular configuration can include a track-etched membrane or a screen material as the quantitation member 94. A track-etched membrane used in the trilaminate configuration of the subject device can be useful as an overflow member, i.e., to absorb excess volume of plasma transferred to the collection member. Typically, the track-etched membrane, e.g., Cyclopore (Whatman), is disposed between the separation member and the collection member, as it is preferred to employ the properties of the track-etched membrane following separation of cellular components from a blood sample. An additional advantage of the track-etched membrane is that it can serve as a filter to further separate any remaining cellular components which may not be removed from plasma or serum by the separation member or members.

Figure 4B:
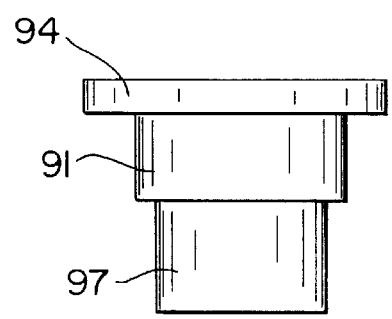
FIG. 4B shows a variation of the trilaminate configuration wherein the screen quantitation member is superimposed over the separation and collection members.

Use of a screen material for the quantitation member 94 can advantageously provide a means for applying consistent and accurate volumes of sample to the collection member 97. This consistent volumetric application can be achieved as a result of the structure of non-absorbent screen material used for the quantitation member 94. Examples of materials useful for a screen quantitation member include synthetic polymeric materials, e.g., nylon, polyester, or the like, which are commonly available having different pore sizes. For example, SEFAR manufactures a plurality of polyester screens under the numerical designation 7-16/8; 7-5/2; 7-105/52; 7-280/44; 7-2F777; and 7-200/44. Nylon screens available from SEFAR include those designated 3-10/2; 3-5/1; and 3-20/14. A variation of this trilaminate configuration as shown in FIG. 4B, includes a device having a screen quantitation member 94 preferably disposed to overlay both the separation member 91 and collection member 97.

Use of a screen material can also have the advantage of serving as an indicator of minimum volume. A minimum volume of liquid sample can be indicated and applied to the device by calibrating relative distance or area of saturation on the overflow member. Accordingly, if a saturation spot does not reach a particular sized area on the overflow member, more sample may be necessary to provide a minimum volume of serum to the collection member for accurate measurement or determination of analyte.

Figure 4C:
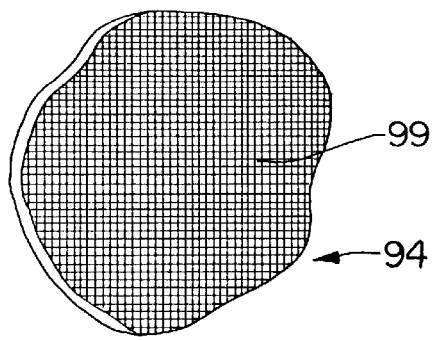
FIG. 4C shows an enlarged elevated view of a quantitation member formed from a screen material.

As shown in FIG. 4C, which is a magnified view of the pore structure forming the screen material of the quantitation member 94, liquid applied to the screen 94 spreads to cover the surface of the screen material and thereby distributes evenly into the pores 99 of the screen, formed by the cross-hatching structure of the screen material. Each of the pores can contain a fixed volume of liquid which is then absorbed onto the separation member 92 and collection member 97 disposed below the quantitation member 94.

Preferably, the separation member 91 has an upper face 92 which has a surface area smaller than the bottom face 96 of the quantitation member 94 and is smaller than the surface area of the spread liquid which is disposed onto the screen. Thus, when liquid sample is applied to the upper surface 95 of the quantitation member 94, the liquid spreads to cover an area larger than the surface area of upper face 92 of separation member 91. Therefore, only liquid sample contained in the pores of the screen material of quantitation member 94, which directly overlay the top surface of the separation member 91, is delivered to the collection member 97.

Figure 4D:
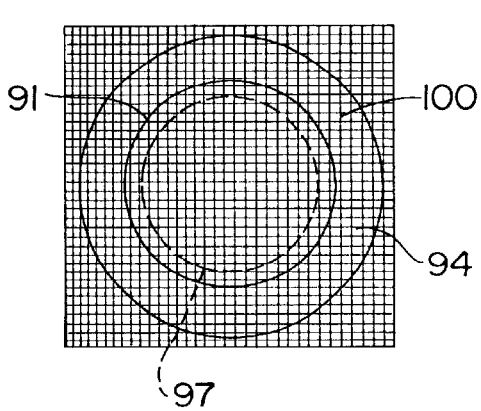
FIG. 4D shows a top plan view of a third embodiment (trilaminate variation of a multilaminate configuration) of a device according to the subject invention.
Figure 4E:
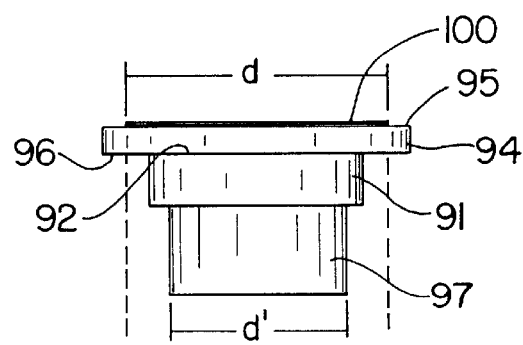
FIG. 4E shows a side view of a third embodiment (trilaminate variation of a multilaminate configuration) of a device according to the subject invention, illustrating the quantitative function achieved by the screen/collection member interface.

As shown in FIG. 4D, the liquid sample 100 spreading onto the quantitation member 94 has a surface area larger than the separation member 91 and the collection member 97 (shown in phantom). This is further illustrated in FIG. 4E, showing the liquid sample 100 covering an area having a diameter d which is larger than the width d' of the separation member 91 or collection member 97.

Figure 4F:
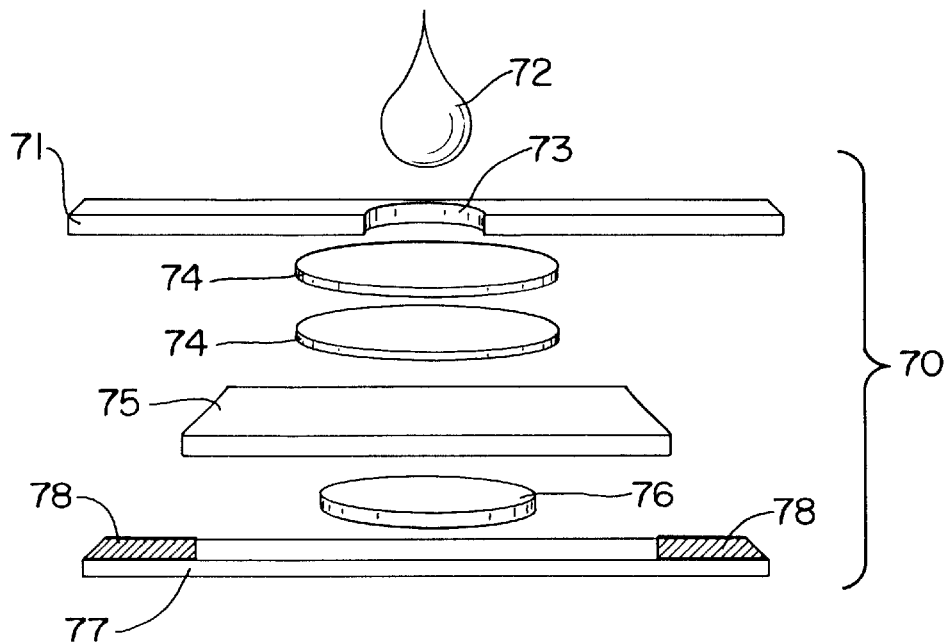
FIG. 4F shows an exploded perspective view of a multilaminate configuration of an embodiment of the subject invention comprising separation members, including an overflow member and a collection member adhered between cover members.
Figure 4G:
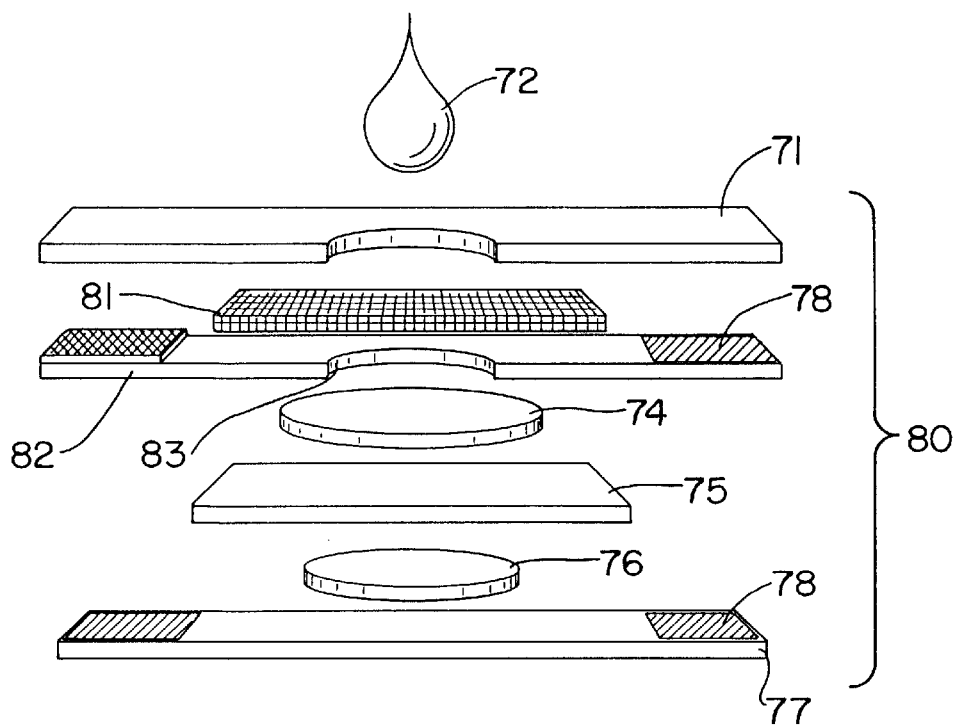
FIG. 4G shows an exploded perspective view of a multilaminate configuration of an embodiment of the subject invention comprising a screen member and an aperture liner member.

FIGS. 4F and 4G show variations of the multilaminate configuration having more than three members constituting the subject device. These are shown in exploded perspective view to illustrate each layer. In FIG. 4F, a multilaminate device 70 is shown comprising a top cover sheet 71 which can be made from a non-porous material, e.g., a polymer or plastic which is typically non-absorbent and non-permeable (e.g., Adhesive Research 7843 plastic; Adhesive Research, Inc., Glen Rock, Pa.). The cover sheet 71 is shown as a sectional view. Sample 72, e.g., a drop of blood, is applied to the top face of the device so that it crosses cover sheet 71 through an aperture, perforation, or pore 73 formed thereon prior to construction of the laminated device.

The multilaminate configuration of the device as shown in FIG. 4F further comprises a separation member 74 which serves to separate and retain an undesired component, e.g., red blood cells, yet allow passage therethrough of a desired component, e.g., serum or plasma. FIG. 4F shows a device comprising two superimposed separation members 74. The separation members 74 can be the same or different materials, and are preferably independently selected from commercially available filter material described herein, e.g., GF 24, HemaSep V, Biodyne B, or the like.

In addition, the multilaminate device 70 comprises an overflow member 75 which can serve to absorb excess volume of liquid sample. The excess can be absorbed from liquid flowing from the separation member disposed in contact with the overflow member, or can absorb excess serum which oversaturates a collection member 76, contactingly disposed below the overflow member. The overflow member 75 can be made from filter material as described herein for a separation member. However, it is preferable to provide an overflow member which is equal to or greater in size than the separation member in order to function as an absorber of excess volume. The overflow member is preferably Cyclopore (Whatman).

The collection member 76 can also be made from material as described herein for a collection member used in other configurations of the subject device. Particular examples of materials that can be used as a collection member are Biodyne B or Ahlstrom 319.

The overflow member 75 can also be a screen material, having structure and properties as described herein. A non-permeable plastic or polymer can also be used to form the bottom layer or coversheet 77 of the subject device. Preferably, a coating of adhesive 78 can be applied to an inner face of coversheet 71 or 77 so that the cover sheets adhere together around the periphery of the other members. In one embodiment, adhesive can be omitted from one edge area so that the coversheets 71 and 78 do not permanently adhere at a particular location to facilitate removal of the collection member 75 from the unitary device.

In FIG. 4G a variation of the multilaminate configuration is illustrated, showing a device 80 according to the subject invention having a separation member 74, and overflow member 75, collection member 76, and top and bottom coversheets 71 and 77, respectively, as in FIG. 4F. However, this variation of the multilaminate configuration comprises an application or screen member 81 for evenly spreading the liquid sample, and an additional impermeable layer 82 which can serve as a liner for the screen member 81. Aperture or perforation 83 provided in layer 82 provides for fluid communication between screen member 81 and separation member 74. Further variations can include an additional screen member 81 or additional separation members 74.

Figure 4H:
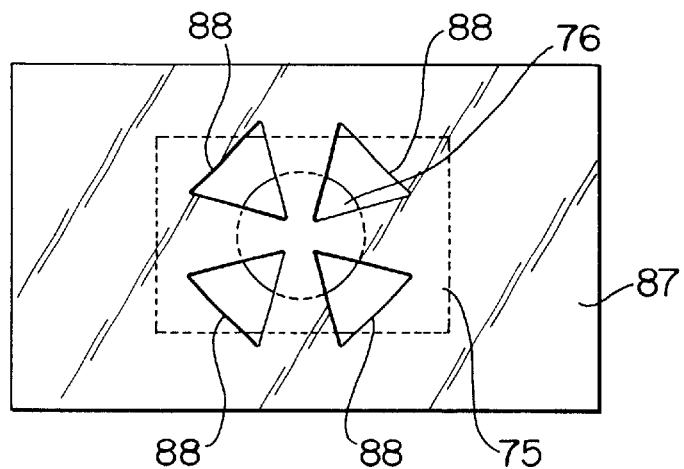
FIG. 4H shows an elevated view of a back face of a multilaminate configuration of the subject invention, illustrating a cut-out area for drying and removal of the collection member.

The embodiments of FIGS. 4F and 4G show a solid bottom coversheet 77. However, to facilitate drying of the collection member, which is advantageous in collecting substantially all of the separated screen or plasma from the sample, the bottom coversheet can be notched or apertured to provide communication between the collection member and the ambient air. The aperture or notch in the bottom coversheet can be various designs, but should provide the stated communication with ambient air while being capable of retaining the collection member in its position. A notch design which achieves this, and further allows access to the collection member for its removal from the device for conducting analysis on the collected serum is shown in FIG. 4H. In FIG. 4H, bottom coversheet 87 has a plurality of cut-out areas 88 which provide ambient air communication to the collection member 76 and overflow member 75, shown partially in phantom. It would be understood that other notch designs can also be useful to obtain said results of facilitating drying and accessing for removal of the collection member.

Figure 4I:
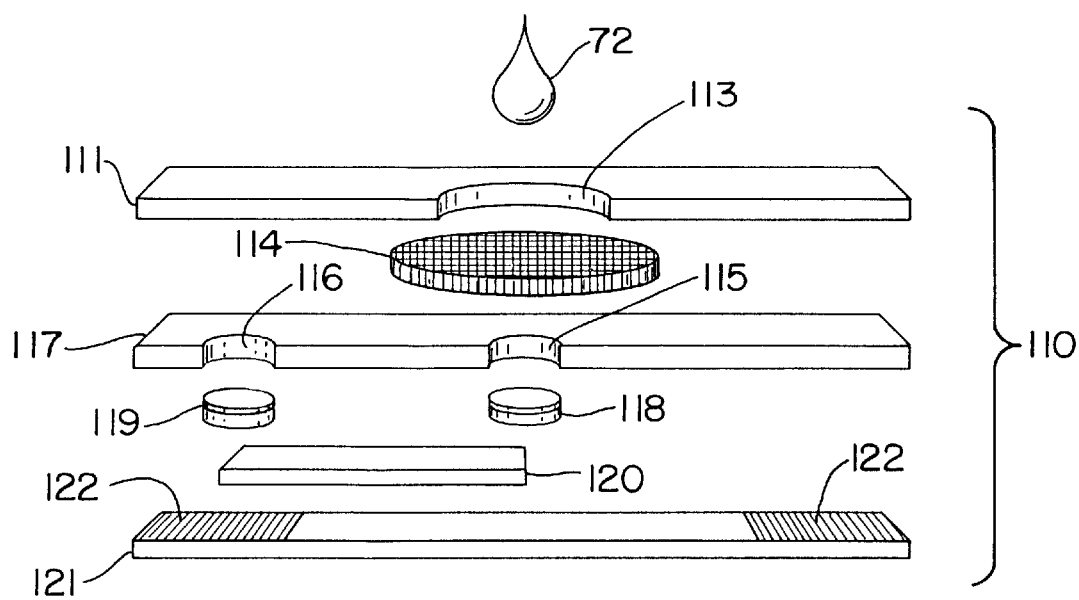
FIG. 4I shows an exploded perspective view of a bridge strip configuration of an embodiment of the subject invention.

In FIG. 4I, a "bridge strip" configuration of the subject invention is shown as device 110 which features an application member 114, an impermeable spacer 117, a separation member 118, a collection member 119, a wicking bridge 120, and top and bottom coversheets 111 and 121, respectively. In this bridge strip configuration, a perforation 113 is present on the top cover sheet 111 such that sample 72 (e.g., a drop of blood) can be applied to application member 114. Application member 114 is used as a target for placing, evenly spreading, and absorbing sample 72. Application member 114 is fluidly connected to separation member 118 via separation member perforation 115, an aperture through impermeable spacer 117. Thus, a portion of applied sample 72 can be delivered from application member 114 through separation member perforation 115 to separation member 118. Separation member 118 can be any device that selectively retains cellular components from sample 72 and delivers non-cellular components of sample 72 to wicking bridge 120, shown in FIG. 4I as a strip of material positioned just below spacer 117 abutting member 118 (e.g., at the bottom face of member 118). Wicking bridge 120 can take the form of any device that fluidly connects separation member 118 to collection member 119 such that a portion of applied sample 72 can flow from separation member 118 to collection member 1 19, on which it can be retained until analysis. The bottom of device 110 is formed by bottom cover sheet 121. Sheet 121 can include an adhesive 122 at the edges of its top face such that sheet 121 can adhere to top cover sheet 111 and form a casing around the other components of device 110. Similarly, the bottom face of top cover sheet 111 can have an adhesive such that sheet 111 can adhere to bottom cover sheet 121.

The components of bridge strip configured devices such as device 110 can be similar to those previously described for the other configured devices within the invention. For example, cover sheets 111 and 121 can be any type of material that can form a substantially impermeable barrier around application member 114, separation member 118, collection bridge 119, and wicking bridge 120. In preferred embodiments sheets 111 and 121 are comprised of plastic. In more preferred embodiments sheets 111 and 121 are comprised of a clear, flexible plastic having adhesive on one side (face) such as adhesive plastic 7843 (Adhesive Research, Inc.). Perforation 113 can be any opening through which a sample can be applied to application member 114. Typically, it takes the form of a round hole punched through top cover sheet 111 having a diameter slightly smaller than member 114.

Application member 114 can be any device that can receive, absorb, and deliver a sample (e.g., a blood drop). It is preferably sized and shaped for facilitating application of a blood drop. For example, it can be round with a diameter of about between 9.5 and 12.7 cm (⅜–½ inch). In preferred embodiments, it is a polyester screen material such as 7-2F777 (SEFAR).

Impermeable spacer 117 can be device that can engage application member 114, separation member 118, and collection member 119. It is preferably composed of a fairly rigid impermeable material such as plastic (e.g., 0.5 mm thick polystyrene plastic), so that it can securely engage the aforesaid components in a manner where unintended leaching of the liquid sample does not occur (i.e., it defines the fluid connection among members 114, 118, 119, and bridge 120). In preferred embodiments, spacer 117 has two perforations 115 and 116 through its thickness (see FIG. 4I). In these embodiments, separation member perforation 115 is preferably positioned within spacer 117 such that it forms an aperture into which separation member 118 can be inserted such that the top face of member 118 contacts application member 114 and the bottom face of member 118 contacts one end of wicking bridge 120. Similarly, in preferred variations, collection member perforation 116 is positioned on spacer 117 such that collection member 119 can be inserted in to perforation 116 in a manner in which an end of wicking bridge 120 is contacting member 119.

Separation member 118 can be any device that can receive a portion of the sample applied to the device and act as a filter that selectively retains one portion of the sample (e.g., the cellular components) and delivers another portion of the sample (e.g., the non-cellular components containing an analyte of interest). Preferably, separation member 118 is shaped and sized so that it can be placed within device 110 (e.g., within perforation 115). A preferred form for member 118 is a flattened circular piece of material having a diameter just slightly smaller than the diameter of perforation 115 (e.g., about 0.075–0.150 mm smaller). In various embodiments, separation member 118 can comprise a glass fiber filter material, a cellulose filter material, a mixed glass fiber/cellulose filter material, track-etched membranes, or other materials such as filter material for separating blood components (e.g., Hemasep V, Hemasep L, Leukosorb, etc.). In some embodiments separation member 118 can comprise multiple layers of one, two or more of the foregoing materials. In a particularly preferred embodiment, separation member 118 is comprised of a sandwich of GF-24 glass fiber filter material (Schleicher and Schuell) and Cyclopore PET (1.0 micron pore size) polyester track-etched membrane. This sandwich can be cut into circles having a diameter of about 4.65 mm to fit within a perforation 115 having a diameter of about 4.75 mm.

Wicking bridge 120 can take the form of any device that can receive a portion of a liquid from one component of device 110 (e.g., separation member 118) and transfer the portion to another component of device 110 (e.g., collection member 119). For example, in a preferred embodiment, wicking bridge 120 can take the form of a rectangular strip of absorbent material sized (e.g., 4×10 mm for some embodiments of device 110) and positioned on device 110 such that it fluidly connects separation member 118 and collection member 119. Bridge 120 can, for example, be comprised of filter type material. In particularly preferred embodiments, bridge 120 can be formed of a rectangular strip of polyester fiber (e.g., AW14-20 from Pall) or Hemasep L (also from Pall). Materials that selectively retain cellular components of a sample applied to device 110 while allowing non-cellular components to flow through are preferred to prevent any cellular components that have passed through separation member 118 from being delivered onto collection member 119.

Collection member 119 can be any device that can receive, absorb, and retain a quantitative portion of the sample applied to device 110 after the sample has passed through separation member 118 and wicking bridge 120. Preferably, collection member 119 is shaped and sized so that it can be placed within device 110 (e.g., within perforation 116). A preferred form for collection member 119 is a flattened circular piece of material having a diameter just slightly smaller than the diameter of perforation 116 (e.g., about 0.075 to 0.150 mm smaller). In various embodiments, collection member 119 can comprise glass fiber, cellulose, polypropylene, nylon, polyester, polyethersulfone, composites of natural and synthetic materials, nitrocellulose, polyethylene, and/or other suitable materials. In some embodiments collection member 119 can comprise multiple layers of one, two or more of the foregoing materials. In a particularly preferred embodiments, collection member 119 is comprised of a sandwich of two or more of APFF glass fiber filter material (Millipore), Biodyne B (0.45 micron) modified nylon material and BFC-180 cellulose material (Whatman).

In preferred embodiments, collection member 119 is substantially free of any chemical or biological reactants used for analyzing an analyte in the sample applied to device 110. Such analytical reagents are preferably not applied to collection member 119 so that analytes on collection member 119 can later be eluted and analyzed (e.g., at a clinical laboratory) without interference caused by contaminating chemicals or biologics. Collection member 119 can, however, be pre-treated with a preservative or stabilizer to enhance stability or "shelf-life" of the collected portion of the sample or can be treated with a reagent to facilitate the release of the analytes from the member during the elution process. For example, devices intended for use in a protein assay can include a collection member that is pre-treated with a reagent formulated to improve the stability of a protein in the sample. Other preservatives or stabilizers that can be used in the subject device include antioxidants, carbohydrates, buffers, other proteins, or the like, which are known in the art to provide a preservative or stabilizing effect on a biological sample. The release of the analytes from the collection pad can be enhanced with a pre-treatment of the collection member of a variety of surfactants.

In more preferred embodiments of device 110, collection member 119 is quantitative in that it absorbs and retains a relatively invariant quantity of a sample, independent of the quantity of sample applied to device 110 (i.e., as long as a minimum threshold volume of sample is applied). For example, if device 110 has a minimum threshold volume of 25 microliters, whether 25, 40, or 60 microliters of a blood sample is applied to application member 114 of device 110, collection member 119 will absorb and retain a specific volume (8 microliters for example) of the non-cellular portion of the sample. In other words, in this example, the quantity of sample absorbed and retained by collection member 119 will be roughly the same (i.e., 8 microliters) if more than 25 microliters of a blood sample is applied. The advantage of collection member 119 being quantitative is that accidental overloading of a sample will not deleteriously affect a later determination of analyte concentration. Therefore, materials that become saturated at a useful minimum threshold volume (e.g., between 2 $\mu$l and 25 $\mu$l) are preferred for use as a quantitative collection member. For example, materials such as nylon (e.g., Biodyne B 0.45 micron from Pall) and glass fiber filter material (e.g., APFF from Millipore) are preferred for use in quantitative collection members. A particularly preferred quantitative collection member is comprised of a circular 2 layer sandwich of Biodyne B (0.45 micron) nylon membrane and APFF glass fiber filter material. This particular construction is preferred because it offers superior sample collection and retention properties over a wide variety of parameters. For example, the volume of sample collected and retained is fairly consistent over a range of different applied sample volumes and loading times (i.e., time between application of the sample to the device and recovery of the collection member for analysis). For example, in bridge strip devices having a collection member made of the Biodyne B/APFF sandwich having a diameter of about 4.65 mm, the collection and retention volume is consistently about 7–8 microliters.

Figure 4J:
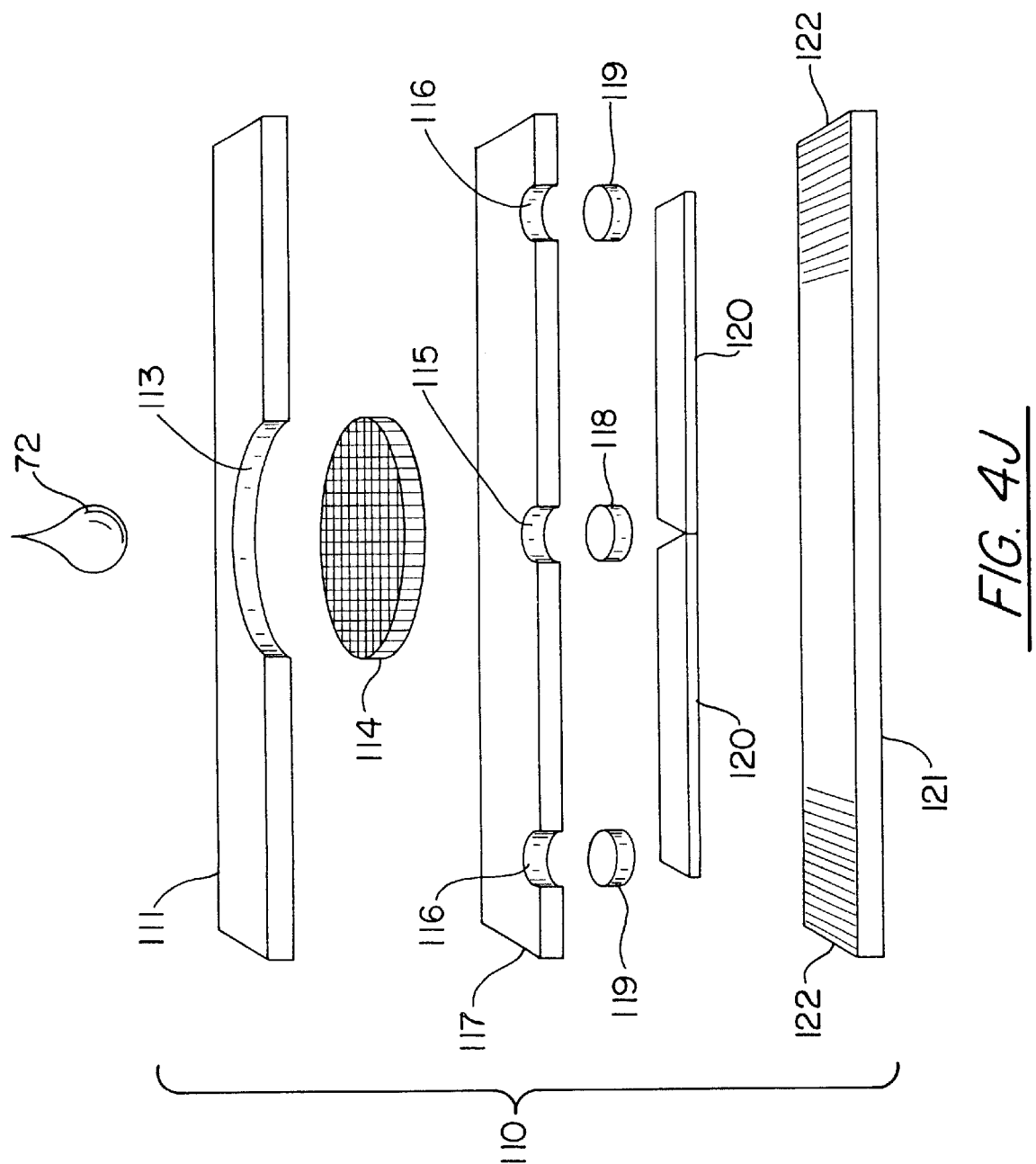
FIG. 4J shows an exploded perspective view of a bridge strip configuration of an embodiment of the subject invention having two quantitative collection members.

In addition to the embodiment illustrated in FIG. 4I, other bridge strip configurations are within the invention. For example, devices of the invention can have more than one of application member 114, impermeable spacer 117, separation member 118, collection member 119, wicking bridge 120, and/or other components of device 119. In preferred variations, as shown in FIGS. 4J and 4K, device 110 can feature multiple collection members 119 and wicking bridges 120. As shown in FIG. 4J, for example, device 110 has two collection members 119 arranged in a line such that one wicking bridge 120 can deliver fluid from separation member 118 tow each of the two collection members 119. In a related embodiment, illustrated in FIG. 4K, device 110 can have three collection members 119 and three wicking bridges 120, each wicking bridge 120 dedicated to delivering fluid from separation member 118 to a particular collection member 119. Still other variations of the foregoing with multiple application members 114, impermeable spacers 117, separation members 118, collection members 119, wicking bridges 120, etc. can be fashioned by one of skill in the art based on the foregoing description. Devices 110 having multiple collection members 119 are preferred for applications where more than one analyte is to be measured from the same sample (e.g. HDL and LDL cholesterol) or to provide a control for error (e.g., standard deviation and like calculations among the different values obtained from analyzing multiple collection members 119 from the same device 110).

Although application member 114, impermeable spacer 117, and cover sheets 111 and 122 are shown in the configuration illustrated in FIG. 4I, other configurations of this bridge-strip design within the invention that do not require these components. For example, a device having application member in fluid communication with separation member 118 which is in fluid communication with collection device 119 via wicking bridge 120, but not having the aforesaid other components is within the invention. Such a device could simply have separation member 118, collection device 119, and wicking bridge 120 fastened together.

Figure 5A:
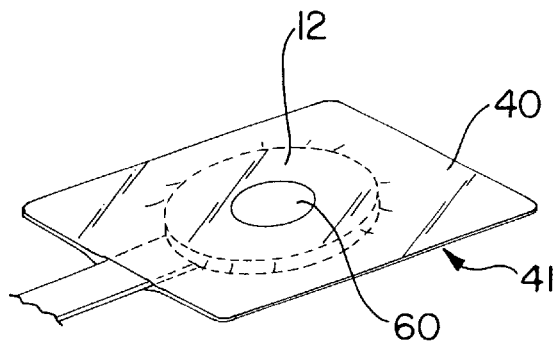
FIG. 5A shows a perspective view of a lateral flow configuration of the subject device having a cover laminated over top and bottom faces of the separation member.
Figure 5B:
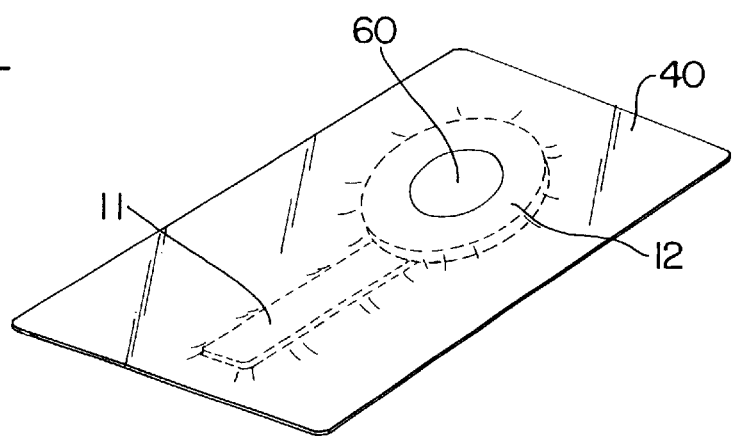
FIG. 5B shows a perspective view of a lateral flow configuration of the subject device having a cover laminated over top and bottom faces of the separation and collection members.
Figure 5C:
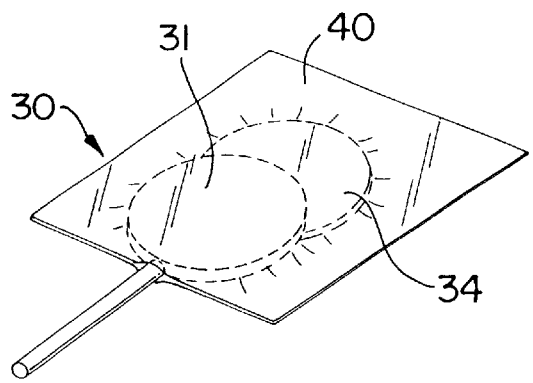
FIG. 5C shows a perspective view of a dual pad configuration of the subject device having a cover laminated over top and bottom faces of the separation member and collection member, having the wicking member extending therefrom.

A preferred device for any of the configurations described herein can include a cover sheet or casing for protecting the absorbent collection or separation members (e.g., 4F–4K). See additionally, for example, FIGS. 5A–5C, which illustrate cover sheets included with the lateral flow and the dual pad configurations. In the lateral flow configuration, the covered subject device 41 includes a cover sheet 40 layered over the top and bottom faces of separation member 12 (FIG. 5A) or, more preferably, a cover sheet 40 layered over separation member 12 and collection member 11 (FIG. 5B). These are shown as having an aperture or perforation 60 in at least one cover sheet.

In a preferred embodiment for the dual pad configuration (FIG. 5C), the subject device includes cover sheet 40 layered over the top and bottom faces of separation member 31 and collection member 34. In one embodiment, cover sheet 40 comprises two separate sheets superimposed over and adhered to one another to completely encase the collection member or separation member (or both) of the subject device. It would be understood that the cover sheet can be formed by folding over a single sheet onto itself to form a double layer.

While a maximum size for the cover sheet can be determined as a matter of convenience of handling, at a minimum, the preferred cover sheet provides complete enclosure of these members in order to provide for proper migration of liquid sample and saturation of the collection member. Thus, for a lateral flow or single pad configuration, using a 6 mm diameter collection member, two 2.54 cm (1 inch) square sheets can be used. Alternatively, a rectangular sheet approximately 2.54 cm (1 inch) wide by approximately 3.8–5.1 cm (1.5–2 inches) long can be used to completely cover the separation member and elongate collection member.

For a dual pad configuration employing an approximately 6 mm diameter separation member and an approximately 6 mm diameter collection member, cover sheets approximately 2.54×3.8 cm (1×1.5 inches) is preferred. This allows for substantially complete closure of the sheets around the separation and collection members, while allowing the wicking member to extend from the cover sheet to facilitate collection of sample.

Any non-porous material, e.g., a polymeric or plastic material, can be used to form the cover sheets. To facilitate closure of the sheets around the perimeter of the collection or separation/collection members, an adhesive-backed plastic sheeting, which does not affect test results, can be used and cut to appropriate size for use. Such plastic sheeting material and adhesive material are well-known in the art. Moreover, the cover sheet advantageously functions to hold together the separate components of the subject device as a single unit. More preferably, an adhesive which can be released for removal of a collection member from therebetween can be used. For example, adhesive plastic 7843 (Adhesive Research, Glen Rock, Pa., USA) can be employed.

Figure 6A:
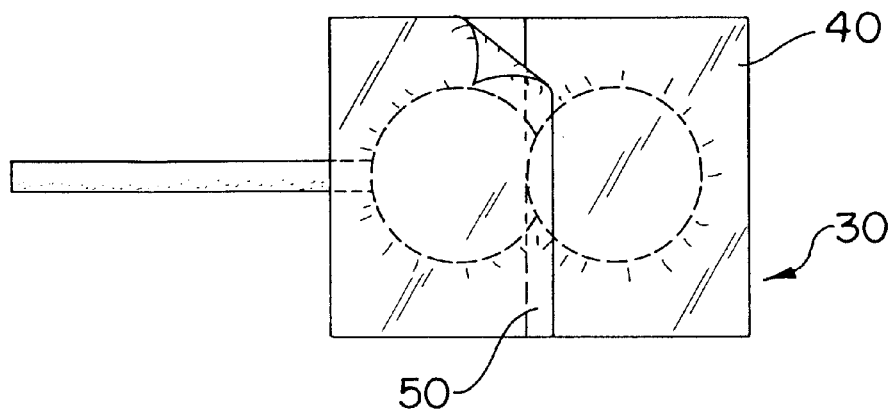
FIG. 6A shows an elevational view of a device according to the subject invention, illustrating a separable flap formed in one cover sheet for facilitating removal of a collection member.
Figure 6B:
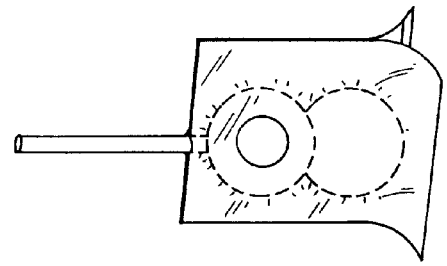
FIG. 6B shows an elevational view of a device according to the subject invention illustrating a separable flap formed by patternly disposed adhesive on the cover sheets which adheres the sheets together around the separation member, but allows separation of the sheets around the collection member.

In one alternative embodiment, which is illustrated in FIGS. 6A and 6B, the sheets 40 are formed so as to provide a flap 50 on one side of the device 30 to facilitate release of the adhesive. In a preferred embodiment, as shown in FIG. 6B, adhesive is caused to be disposed on only a portion of the cover sheets such that a flap is formed at one end of said cover sheets, leaving one end unadhered and easily opened for removal of the collection member from between the cover sheets. The patternly disposed adhesive can be selectively applied at the end of the cover sheets which cover the separation member and the wicking member so that adherence is only made at the end covering these members. In the alternative, cover sheets having adhesive coated on their entire inner surface can be provided, and removal of adhesive from the collection member end can be carried out prior to adhering the cover sheets together.

Figure 7:
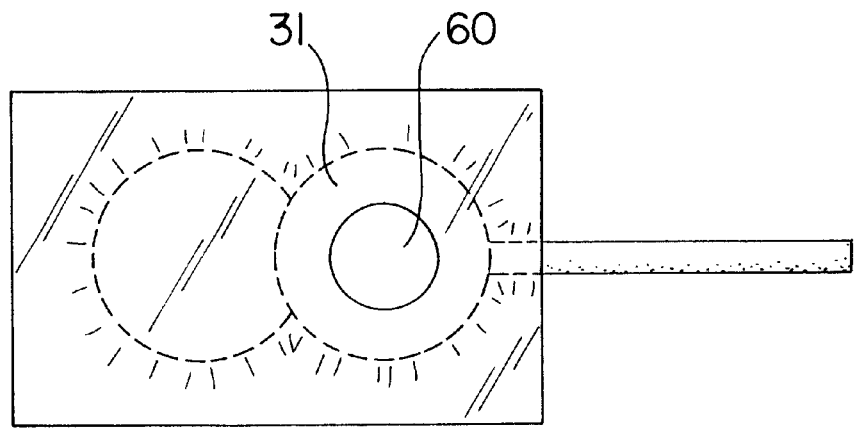
FIG. 7 shows an elevational view of an embodiment of the subject invention illustrating a perforation formed in the cover laminate.

Also on one side of the cover sheets, shown in FIG. 7, preferably a top side or a side opposite the flap 50, is a perforation or aperture 60 formed in the cover 40. This perforation 60, which is preferably formed in the portion of the plastic cover sheet to overlay the separation member, permits exposure to the air of the separation member in the dual pad configuration to facilitate or expedite drying of the sample which can be advantageous for preventing spill-over of undesired sample components (cells) onto the collection member, as well as application, transport, and analysis of the sample. In a preferred embodiment, the diameter of the perforation is approximately 60–75% of the diameter of the collection member. Alternatively, the perforation or aperture can be a plurality of holes formed within substantially the same diameter of the aperture shown in the Figures.

It would be readily understood by those of ordinary skill in the art that other dimensions could be used for any of the components forming the subject device, as long as those other dimensions are used routinely and consistently.

Figure 8A:
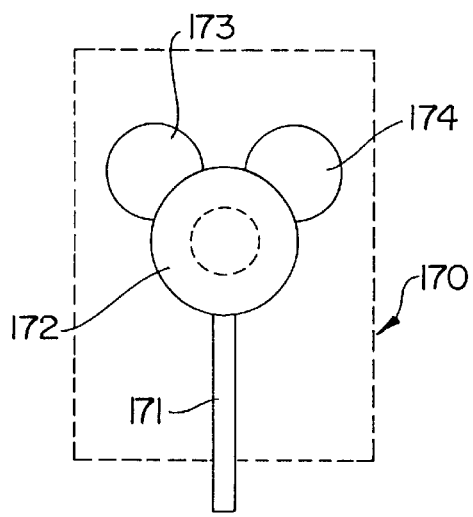
FIGS. 8A–8D show alternative configurations of a device according to the subject invention having a plurality of collection or separation members.
Figure 8B:
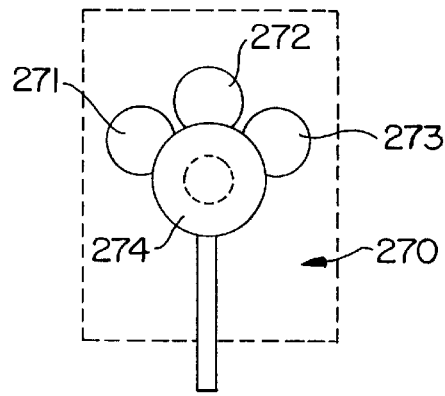

Variations of the subject device include embodiments having more than one collection member or more than one separation member. Certain of these variations contemplated for the subject invention are shown in FIGS. 8A–8D. For example, FIG. 8A shows a device 170 having a wicking member 171, separation member 172, and a pair of collection members 173 and 174 overlappingly disposed in contact with the separation member, but are positioned separate from each other at acute angles around the periphery of the separation member. FIG. 8B shows an alternative embodiment 270 to the configuration in FIG. 8A wherein three (3) collection members 271, 272, and 273 are overlappingly disposed in contact with the separation member 274.

Figure 8C:
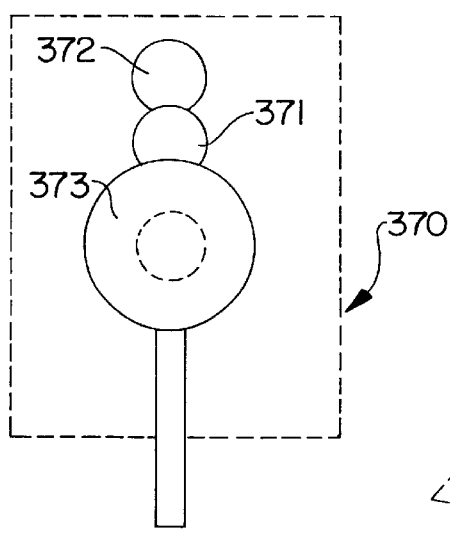

FIG. 8C shows an embodiment 370 wherein two collection members 371 and 372 are disposed sequentially relative to the separation member 373. The first collection member 371 is overlappingly in contact with separation member 373, and the second collection member 372 is in contact with the first collection member 371. Alternatively, this configuration could provide member 371 as a second separation member.

Figure 8D:
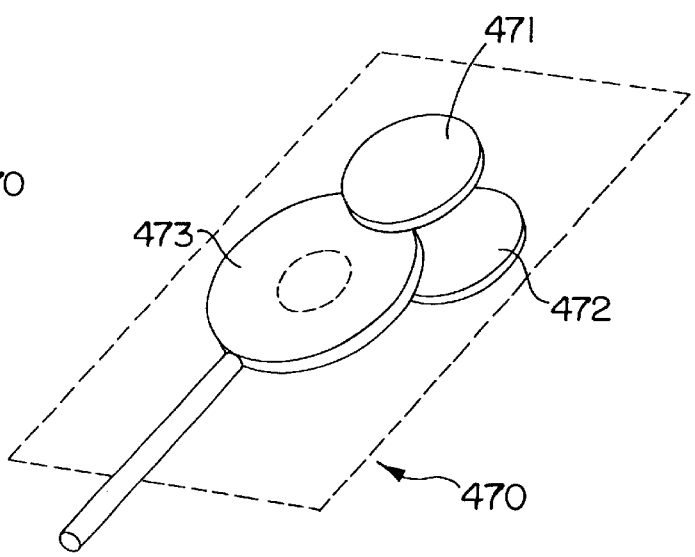
Figure 10:
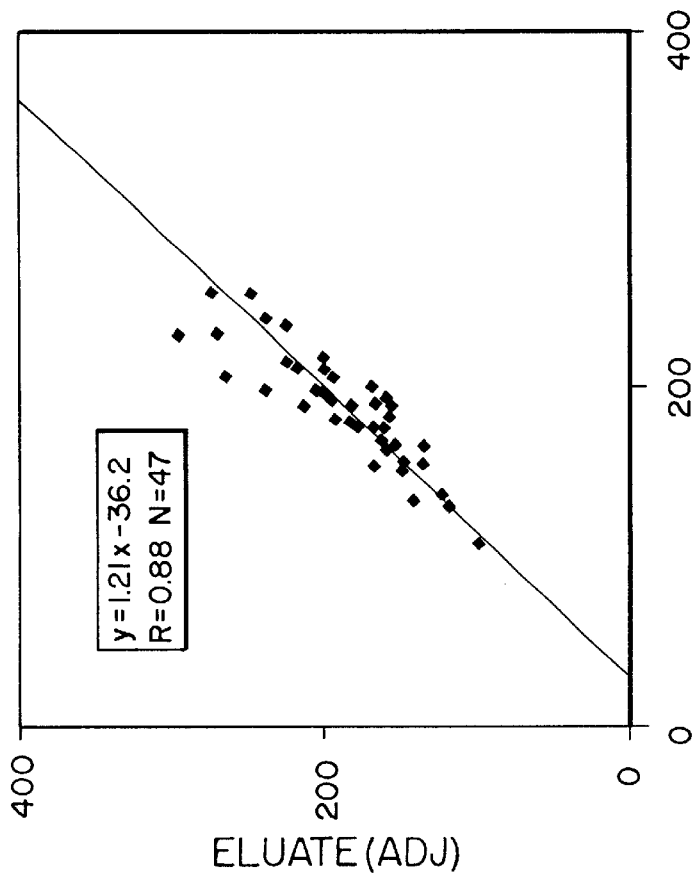
FIG. 10 shows regression analysis results for blood sample eluates (adjusted) vs. neat blood samples analyzed for cholesterol concentration using a single pad configuration of a device according to the subject invention.
Figure 9:
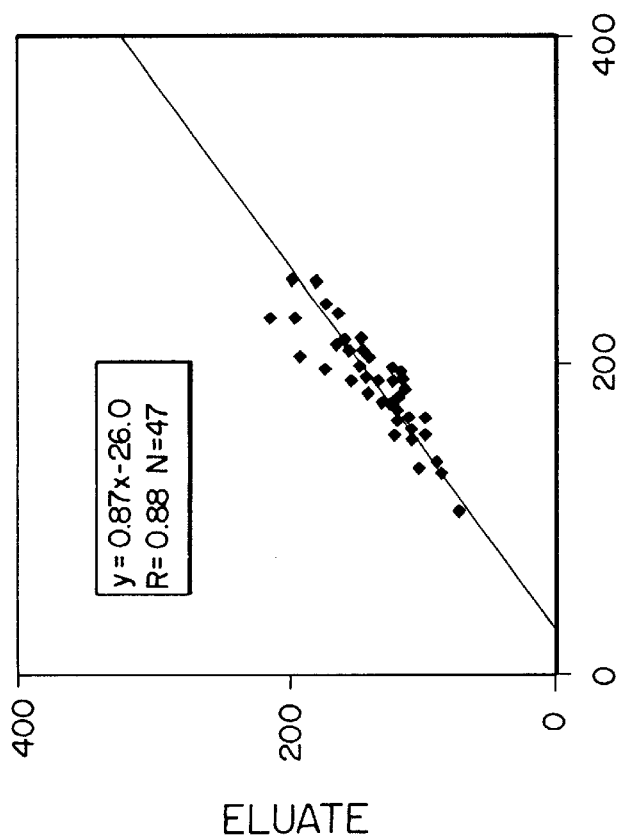
FIG. 9 shows regression analysis results for blood sample eluates vs. neat blood samples analyzed for cholesterol concentration using a single pad configuration of a device according to the subject invention.
Figure 14:
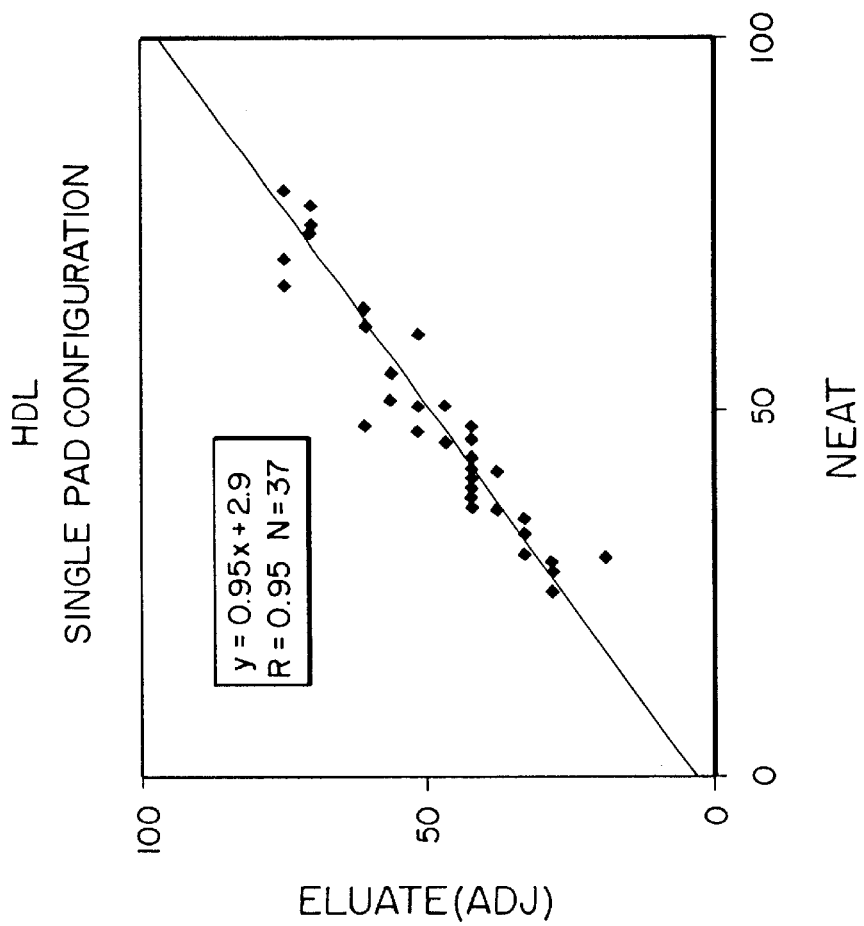
FIG. 14 shows regression analysis results for blood sample eluates (adjusted) vs. neat blood samples analyzed for HDL concentration using a single pad configuration of a device according to the subject invention.
Figure 13:
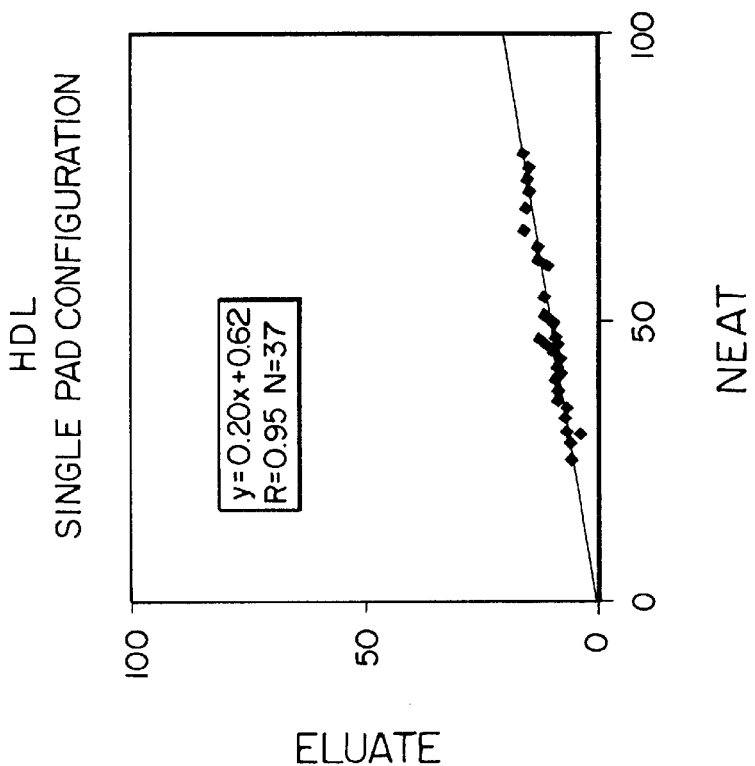
FIG. 13 shows regression analysis results for blood sample eluates vs. neat blood samples analyzed for HDL concentration using a single pad configuration of a device according to the subject invention.
Figure 16:
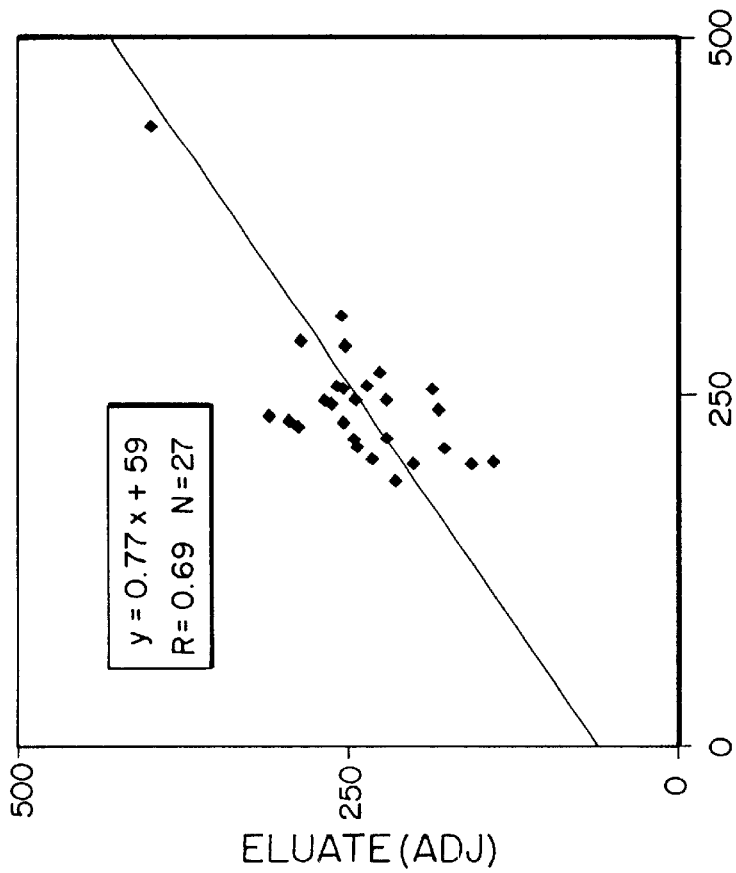
FIG. 16 shows regression analysis results for blood sample eluates (adjusted) vs. neat blood samples analyzed for fructosamine concentration using a single pad configuration of a device according to the subject invention.
Figure 15:
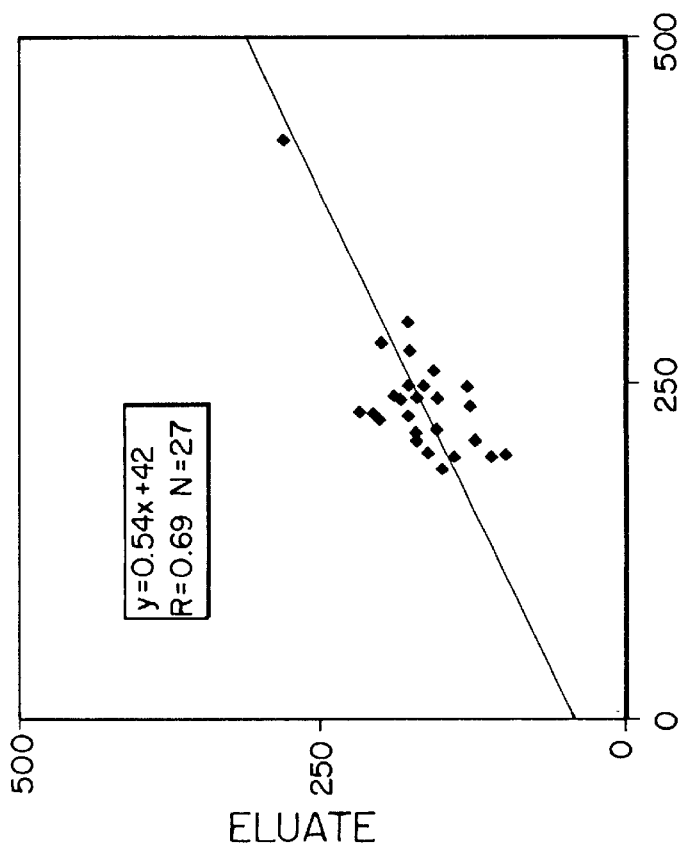
FIG. 15 shows regression analysis results for blood sample eluates vs. neat blood samples analyzed for fructosamine concentration using a single pad configuration of a device according to the subject invention.
Figure 18:
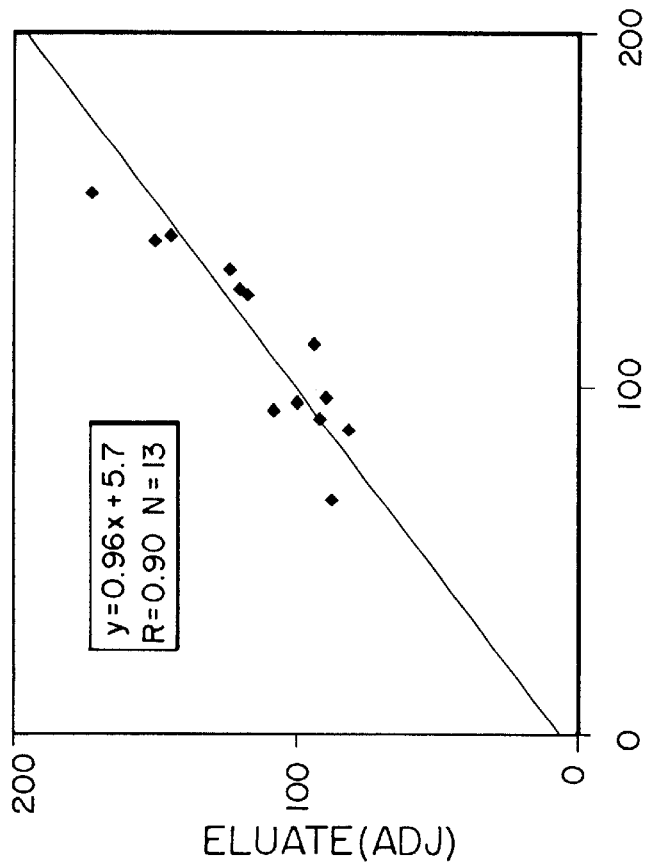
FIG. 18 shows regression analysis results for blood sample eluates (adjusted) vs. neat blood samples analyzed for direct LDL concentration using a single pad configuration of a device according to the subject invention.
Figure 17:
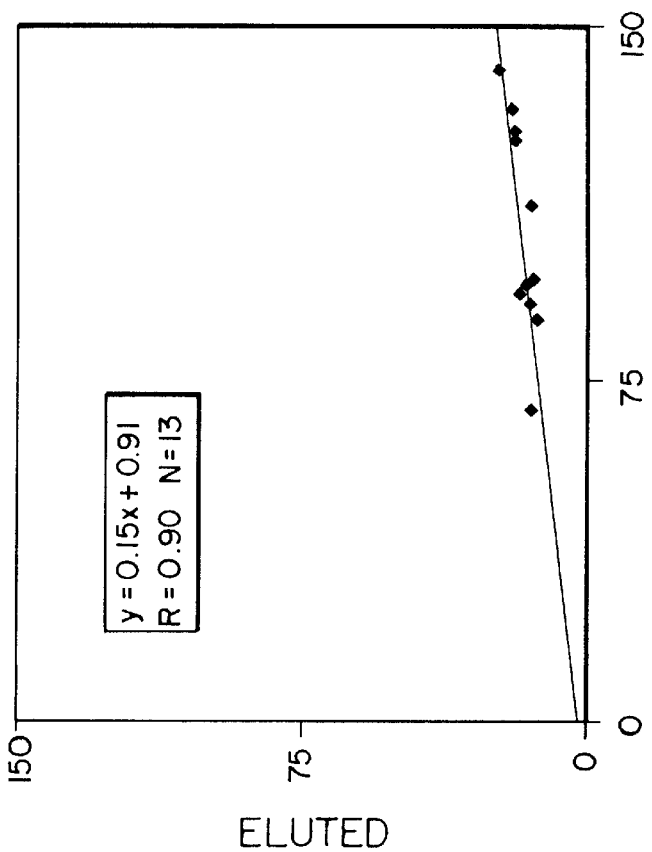
FIG. 17 shows regression analysis results for blood sample eluates vs. neat blood samples analyzed for direct LDL concentration using a single pad configuration of a device according to the subject invention.
Figure 20:
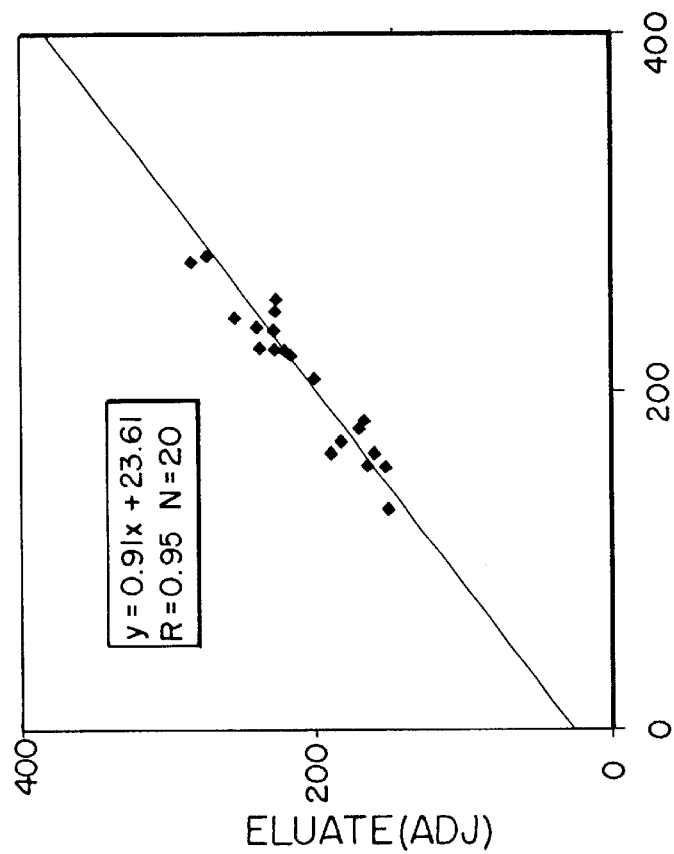
FIG. 20 shows regression analysis results for blood sample eluates (adjusted) vs. neat blood samples analyzed for cholesterol concentration using a dual pad configuration of a device according to the subject invention.
Figure 19:
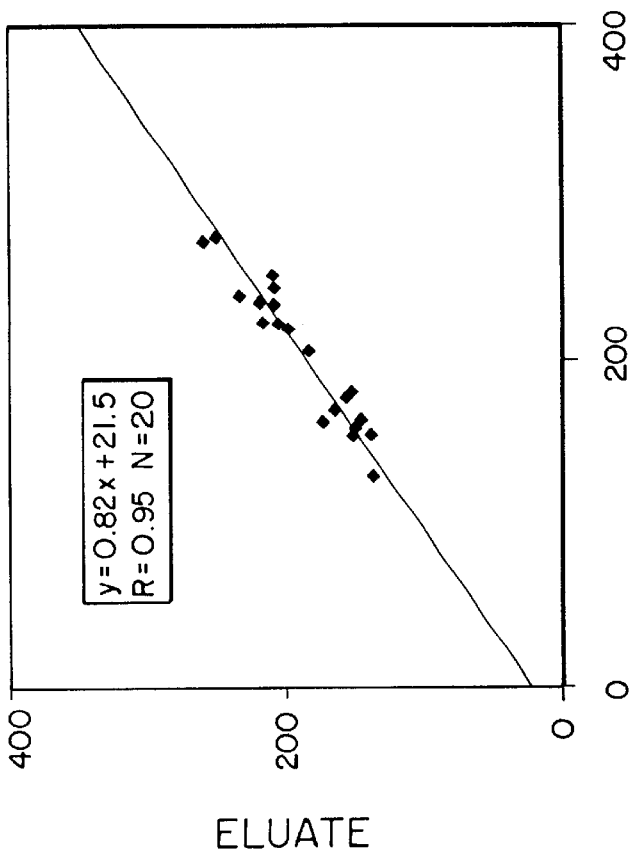
FIG. 19 shows regression analysis results for blood sample eluates vs. neat blood samples analyzed for cholesterol concentration using a dual pad configuration of a device according to the subject invention.
Figure 22:
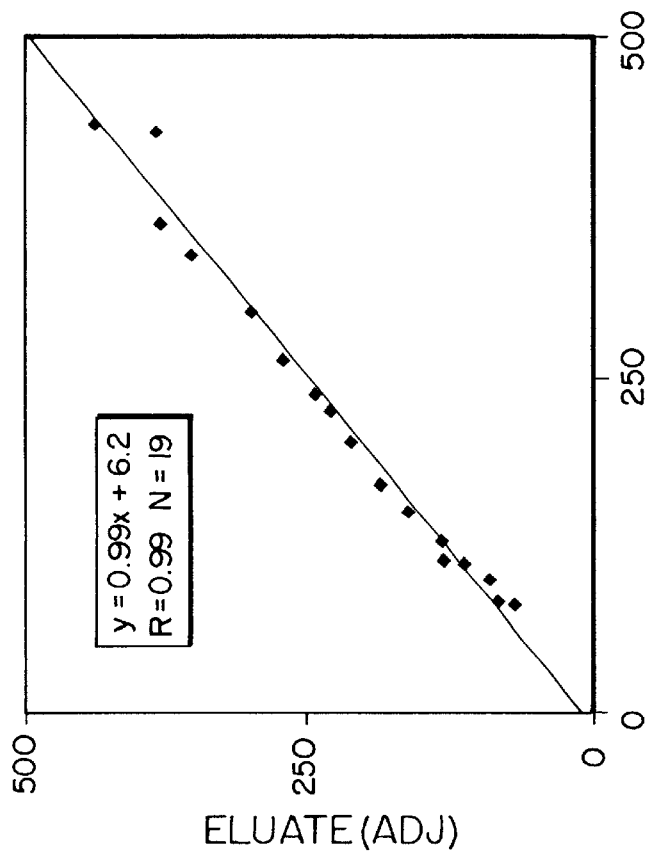
FIG. 22 shows regression analysis results for blood sample eluates (adjusted) vs. neat blood samples analyzed for triglyceride concentration using a dual pad configuration of a device according to the subject invention.
Figure 21:
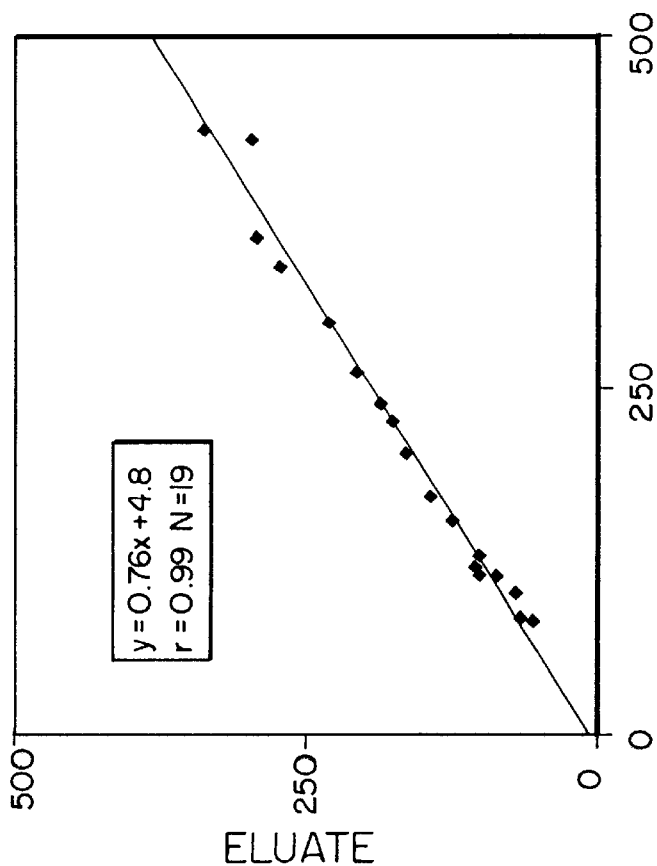
FIG. 21 shows regression analysis results for blood sample eluates vs. neat blood samples analyzed for triglyceride concentration using a dual pad configuration of a device according to the subject invention.
Figure 24:
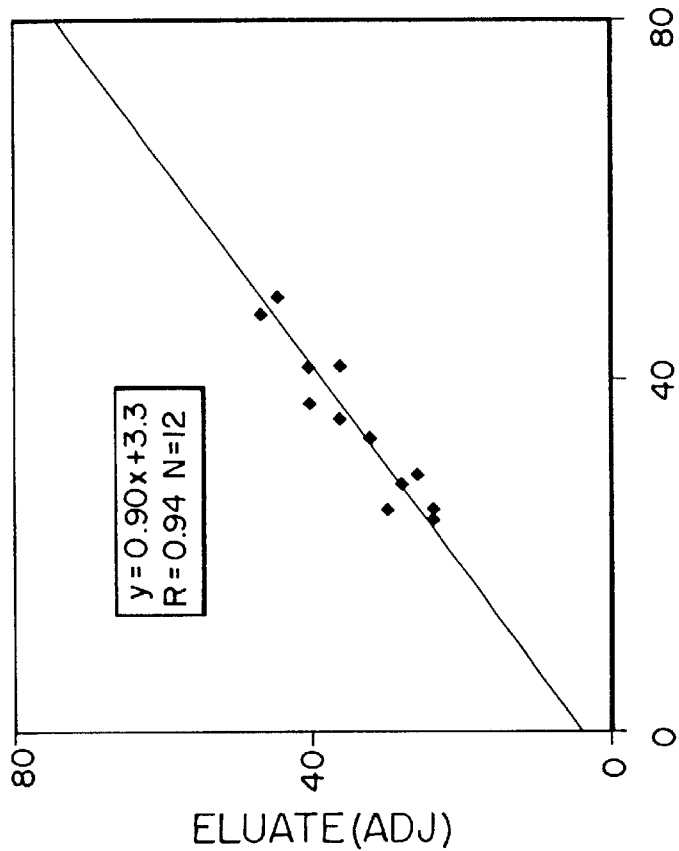
FIG. 24 shows regression analysis results for blood sample eluates (adjusted) vs. neat blood samples analyzed for ALT concentration using a dual pad configuration of a device according to the subject invention.
Figure 23:
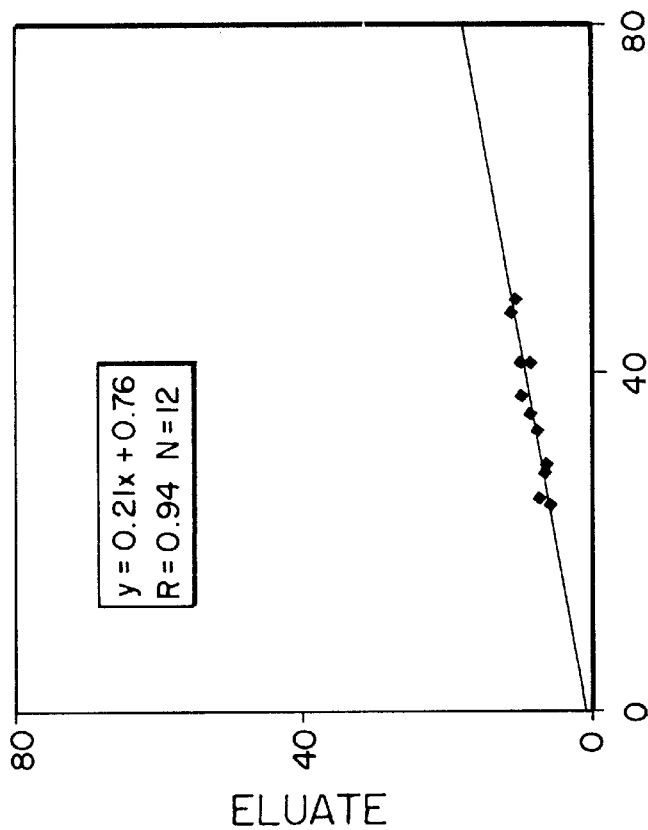
FIG. 23 shows regression analysis results for blood sample eluates vs. neat blood samples analyzed for ALT concentration using a dual pad configuration of a device according to the subject invention.

A further variation 470 shown in FIG. 8D shows a pair of collection members 471 and 472 overlappingly disposed in contact with opposing faces of the separation member 473.

To assemble the components of the lateral flow configuration of the subject device, the following steps are conducted:

(a) Peel the cover from the adhesive backing on the first plastic sheet, which includes the circular opening;

(b) Center the separation member, smooth side toward the adhesive side of the first plastic sheet, placing said member in a position to completely cover the circular opening, and pressing down firmly to secure said member in place.

(c) Place one end of the quantitation or wicking member in the center of the collection member such that the "tail" extends radially from the separation member. Cover the collection member and at least part of the quantitation or wicking member with a second sheet of the adhesive-backed plastic, superimposing the second and first sheets.

(d) Press down firmly to compress the quantitation or wicking and collection members at the point of contact. Secure adhesive around entire assembly with special attention given to the area immediately surrounding the collection member.

Thus, the lateral flow configuration is assembled "upside down", i.e. building the layers forming the device from the top face to the bottom face.

The single pad configuration can be assembled in an identical manner except that it includes, prior to application of the second cover sheet, providing a wicking member which is disposed to abut the separation member, diametrically opposite to the collection member.

For preparing a device having a dual pad configuration, similar steps are taken except that the device is assembled in a "right-side-up" manner, i.e., building the layers forming the device from the bottom face to the top face. Specifically, the collection member is first placed toward the center of an adhesive backed cover sheet forming the back face of the device, ensuring that the sheet will encase the collection member. A separation member is then overlapped onto the collection member and a quantitation or wicking member abutted thereagainst. A second, top cover sheet is then super-imposed over the first cover sheet and adhered thereto, ensuring that the entire separation member is covered by the cover sheets and that the aperture in the top cover sheet is positioned over the separation member. It is preferred that the top and bottom cover sheets are adhered together over the two faces of the device and are adhered together at least at the quantitation or wicking member end. Preferably, the adherence is from the end covering the quantitation or wicking member, extending about half the length of the cover sheet so as to provide a non-adhered section at the end of the cover sheets covering the collection member. An advantage to having adhesion on about half the area of the cover sheets is to facilitate removal of the collection member from the rest of the device for transporting the collection member to a laboratory for analysis.

The multilaminate configuration and bridge strip configuration can be assembled by using a cover sheet as a base and layering the component members over one another in a desired configuration. The multilaminate configuration can be assembled from top to bottom or from bottom to top. Apertures or other cut-out areas or shapes of the component members are preferably pre-formed prior to assembly. Preferred layering sequences are illustrated in FIGS. 4A–4K.

The subject method for using a device according to the subject invention as described herein comprises applying, either directly or indirectly, a liquid sample to the separation member, allowing the liquid sample to separate thereon and substantially saturate the collection member, allowing the separation member and collection members to dry, for at least two hours, preferably overnight, at room temperature after collection of the sample, and then shipping, typically by mail, the dried separation and collection members to a facility for analysis.

Use of configurations of the subject device comprising a capillary tube as a quantitation or wicking member include contacting a liquid sample to the free end of the quantitation or wicking member and allowing the sample to migrate to and substantially saturate the separation member. The remaining steps are substantially identical for all other configurations of the subject device.

Clinical analysis using the device of the subject invention is achieved through a series of steps that allow for the specific quantification of sample components as captured by the collection member.

Specifically, when the device and sample are received at the analytical facility, the dried collection member is removed from the device assembly, components of interest are extracted from the collection member. Extraction of the analyte is typically achieved by eluting the analyte of interest into a liquid eluent, e.g., water, aqueous buffer, reactive reagent, inorganic or organic solvent, or the like. Analysis of the extract is usually performed by established clinical methodologies, with values adjusted according to the dilutions made. Analyses of blood components (analytes) from a sample of whole blood using the subject device can include, but are not limited to, determining presence or absence (and if present, quantification of) total cholesterol, triglyceride, bone alkaline phosphatase, high density lipoprotein (HDL) cholesterol, low density lipoprotein (LDL) cholesterol, ALT, glucose and fructosamine. Analyses can be performed with the use of a commercially available blood chemistry analyzer, e.g., Roche Cobas Mira Plus Chemistry Analyzer, using readily recognized modifications of established assay parameters. Results of analyses of samples assayed for certain typically assayed blood components are shown in FIGS. 9–24, demonstrating comparable results using a device of the subject invention versus standard liquid blood sample analysis.

Following are examples which illustrate procedures for practicing the invention. These examples should not be construed as limiting. All percentages are by weight and all solvent mixture proportions are by volume unless otherwise noted.

EXAMPLE

Empirical Results Using Subject Device

Various materials for use as a component of the subject device were shown to successfully absorb separated sample, e.g., serum or plasma, from the wicking or separation member. Optimal plasma migration is obtained when the collection member is positioned to overlap the separation member by approximately 1 mm. Plasma migration was only about 50% as successful when the separation member and collection member abutted to one another rather than over-lapped.

The device performed superiorly when encased in a minimum of about 3.8 cm (1.5") of plastic cover sheet material. Substantially complete enclosure of the device is required for the migration of the serum using a GF24 separation member contacting the collection member.

A low degree of "spill over" was observed using the device of the subject invention. Spill-over is defined here as the migration of red blood cells onto the collection pad immediately following blood application.

Hemolysis was observed after more than 24 hours of drying time when the cover sheets were not perforated. Hemolysis is defined as an overall redness that appears on the collection member over time, distinguishing it from "spill-over" which is evident at the point of contact at the time of blood application. All devices were free of hemolysis on the day of spotting. Overall, the degree of hemolysis is much less with the dual pad configuration than was observed with the single pad configuration.

Hemolysis was shown to be virtually eliminated with the incorporation of the perforation punched into the plastic cover sheet placed directly over the separation or collection member.

In addition, imprecision between replicates is greatly improved with the new dual pad configuration as compared to the single pad configuration. Sensitivity of cholesterol and triglyceride is adequate employing the 30 μl capillary tube as a wicking member and a 0.635 cm (¼ inch) collection member. It is compromised somewhat with the use of the smaller devices, i.e., 20 μl blood: 0.48 cm (3/16") collection pads. A decrease in elution volume would compensate for this loss in sensitivity if a low volume application is necessary.

Sonification vs. shaking studies were performed to determine whether the imprecision between replicate spots could be attributed to incomplete elution of cholesterol from the collection member. Initial data show improvement when sonification is employed.

It should be understood that the examples and embodiments described herein are for illustrative purposes only and that various modifications or changes in light thereof will be suggested to a person of ordinary skill in the art and are to be included within the spirit and purview of this description.

What is claimed is:

1. An apparatus for isolating an analyte from a blood sample, the apparatus comprising:

a separation member for receiving a portion of the blood sample, the separation member comprising a filter that selectively retains cellular components contained within the portion of the blood sample and delivers non-cellular components of the portion of the blood sample containing the analyte;

a wicking bridge fluidly connected to the separation member such that the wicking bridge can receive the non-cellular components of the portion of the blood sample containing the analyte from the separation member, the wicking bridge comprising a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants for analyzing the analyte and comprising a swatch of material that is adapted for absorbing and retaining a specific quantity of the non-cellular components of the portion of the blood sample containing the analyte.

2. The apparatus of claim 1, wherein the separation member comprises a layer of glass fiber filter material and a layer of track-etched membrane.

3. The apparatus of claim 2, wherein the layer of track-etched membrane comprises at least one of polyester and polycarbonate and has a plurality of pores having a mean diameter of about 0.2 to 5.0 micron.

4. The apparatus of claim 3, wherein the track-etched membrane comprises polyester and the plurality of pores have a mean diameter of about one micron.

5. The apparatus of claim 1, wherein the separation member is impregnated with a surfactant.

6. The apparatus of claim 5, wherein the surfactant is a polyoxyethylene sorbitan ester.

7. The apparatus of claim 1, wherein the separation member is impregnated with a protein that reduces adsorption of components of the blood sample to the separation member.

8. The apparatus of claim 7, wherein the protein is bovine serum albumin.

9. The apparatus of claim 1, wherein the separation member is impregnated with an erythrocyte agglutinin.

10. The apparatus of claim 9, wherein the agglutinin is a lectin.

11. The apparatus of claim 9, wherein the agglutinin is an antibody that specifically binds to erythrocytes.

12. The apparatus of claim 1, wherein the wicking bridge comprises a fibrous polyester matrix.

13. The apparatus of claim 1, wherein the quantitative collection member comprises a layer of glass fiber filter material.

14. The apparatus of claim 1, wherein the quantitative collection member comprises a layer of nylon.

15. The apparatus of claim 14, wherein the quantitative collection member further comprises a layer of material selected from the group consisting of glass fiber filter material and cellulose.

16. The apparatus of claim 1, wherein the apparatus comprises a second quantitative collection member, the second quantitative collection member being fluidly connected to the wicking bridge such that the second quantitative collection member can receive the non-cellular components of the portion of the blood sample containing the analyte from the wicking bridge, substantially free of any reactants for analyzing the analyte, and comprised of a swatch of material that is adapted for absorbing and retaining a specific quantity of the non-cellular components of the portion of the blood sample containing the analyte.

17. The apparatus of claim 16, wherein the apparatus comprises a third quantitative collection member, the third quantitative collection member being fluidly connected to the wicking bridge such that the third quantitative collection member can receive the non-cellular components of the portion of the blood sample containing the analyte from the wicking bridge, substantially free of any reactants for analyzing the analyte, and comprised of a swatch of material that is adapted for absorbing and retaining a specific quantity of the non-cellular components of the portion of the blood sample containing the analyte.

18. The apparatus of claim 1, wherein said apparatus further comprises an application member fluidly connected to the separation member, the application member comprising a swatch of material having a plurality of pores for absorbing the blood sample and delivering a portion of the blood sample to the separation member.

19. The apparatus of claim 18, wherein the application member comprises polyester screen.

20. The apparatus of claim 18, wherein the application member is impregnated with a protein that reduces adsorption of components of the blood sample to the application member.

21. The apparatus of claim 20, wherein the protein is bovine serum albumin.

22. The apparatus of claim 18, wherein the application member is impregnated with a surfactant.

23. The apparatus of claim 22, wherein the surfactant is a polyoxyethylene sorbitan ester.

24. The apparatus of claim 18, wherein the application member is impregnated with an erythrocyte agglutinin.

25. The apparatus of claim 24, wherein the agglutinin is a lectin.

26. The apparatus of claim 24, wherein the agglutinin is an antibody that specifically binds to erythrocytes.

27. The apparatus of claim 18, the apparatus further comprising a casing which houses the application member, the separation member, the wicking bridge, and the quantitative collection member; the casing having an opening for applying the blood sample to the application member.

28. The apparatus of claim 27, wherein the casing comprises two pieces of a fluid impermeable plastic material sealed together in an airtight manner such that gas exchange between the ambient atmosphere, the application member, the separation member, the wicking bridge, and the quantitative collection member occurs almost entirely through the opening of the casing.

29. The apparatus of claim 28, the apparatus further comprising an impermeable spacer interposed between the wicking bridge and the application member, the impermeable spacer having a thickness of about 5.0 mm (0.020 inches) and having a first perforation through the thickness for accommodating the separation member and a second perforation through the thickness for accommodating the quantitative collection member.

30. The apparatus of claim 29, wherein the first perforation and the second perforation each have a diameter of about 4.75 mm (0.1875 inches), and the separation member and the quantitative collection member each have a diameter of about 4.65 mm (0.1825 inches).

31. The apparatus of claim 27, the apparatus further comprising an identification label attached to the casing, the identification label for displaying information indicating the source of blood sample.

32. The apparatus of claim 31, wherein the identification label includes a bar code.

33. The apparatus of claim 18, wherein
   the application member comprises polyester impregnated with at least one protein that reduces adsorption of components of blood sample to the application member and at least one agglutinin;
   the separation member comprises a layer of glass fiber filter material and a layer of polyester track-etched membrane;
   the wicking bridge comprises a fibrous polyester matrix; and
   the quantitative collection member comprises a layer of nylon and a layer of glass fiber filter material.

34. An apparatus for isolating an analyte from a blood sample, the apparatus comprising:
   a capillary tube for quantitatively aspirating a specific volume of the blood sample and delivering a specific volume of a portion of the blood sample to the separation member;

a separation member fluidly connected to the capillary tube such that the separation member can receive the specific volume of the portion of the blood sample from the capillary tube, the separation member comprising a filter that selectively retains cellular components of the portion of the blood sample and delivers non-cellular components of the portion of the blood sample containing the analyte;

a wicking bridge fluidly connected to the separation member such that the wicking bridge can receive the non-cellular components of the portion of the blood sample containing the analyte from the separation member, the wicking bridge comprising a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants for analyzing the analyte and comprising a swatch of material that is adapted for absorbing and retaining a specific quantity of the non-cellular components of the portion of the blood sample containing the analyte.

35. A kit for isolating an analyte from a sample of blood, the kit comprising:

an apparatus comprising a separation member for receiving a predetermined volume of the blood sample, the separation member comprising a filter that selectively retains cellular components of the portion of the blood sample and delivers non-cellular components of the portion of the blood sample containing the analyte;

a wicking bridge fluidly connected to the separation member such that the wicking bridge can receive the non-cellular components of the portion of the blood sample containing the analyte from the separation member, the wicking bridge comprising a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants for analyzing the analyte and comprising a swatch of material that is adapted for absorbing and retaining a specific quantity of the non-cellular components of the portion of the blood sample containing the analyte; and a quantitative fluid dispenser for delivering the predetermined volume of the sample of the blood to the separation membrane.

36. The kit of claim 35, wherein said quantitative fluid dispenser is a micropipet.

37. The kit of claim 35, wherein said quantitative fluid dispenser is a capillary tube.

38. A kit for isolating an analyte from a blood sample, the kit comprising:

an apparatus comprising a separation member for receiving an aliquot of the blood sample, the separation member comprising a filter that selectively retains cellular components of the portion of the blood sample and delivers non-cellular components of the portion of the blood sample containing the analyte;

a wicking bridge fluidly connected to the separation member such that the wicking bridge can receive the non-cellular components of the portion of the blood sample containing the analyte from the separation member, the wicking bridge comprising a strip of porous material for transporting the non-cellular components of the portion of the blood sample containing the analyte away from the separation member; and a quantitative collection member fluidly connected to the wicking bridge such that the quantitative collection member can receive the non-cellular components of the portion of the blood sample containing the analyte from the wicking bridge, the quantitative collection member being substantially free of any reactants for analyzing the analyte and comprising a swatch of material that is adapted for absorbing and retaining a specific quantity of the non-cellular components of the portion of the blood sample containing the analyte; and a lancet; and an antiseptic.

39. The kit of claim 38, the kit further comprising:

instructions for using the kit; and a bar-coded identification card.

* * * * *

UNITED STATES PATENT AND TRADEMARK OFFICE
CERTIFICATE OF CORRECTION

PATENT NO. : 6,258,045 B1
DATED : July 10, 2001
INVENTOR(S) : Ray et al.

Page 1 of 1

It is certified that error appears in the above-identified patent and that said Letters Patent is hereby corrected as shown below:

<u>Title page,</u>
Insert -- Raul Sarzo -- as inventor.

Signed and Sealed this

Twenty-ninth Day of January, 2002

Attest:

*Attesting Officer*

JAMES E. ROGAN
*Director of the United States Patent and Trademark Office*